US008579935B2

(12) United States Patent
DeVries et al.

(10) Patent No.: US 8,579,935 B2
(45) Date of Patent: Nov. 12, 2013

(54) TISSUE FASTENERS AND RELATED DEPLOYMENT SYSTEMS AND METHODS

(75) Inventors: Robert B. DeVries, Northborough, MA (US); Kristian DiMatteo, Waltham, MA (US); Roy Sullivan, Millville, MA (US); Marc Tassy, Jr., Framingham, MA (US); Barry N. Gellman, Easton, MA (US); John E. Hutchins, Attleboro, MA (US); John B. Golden, Norton, MA (US); Kurt A. E. Geitz, Sudbury, MA (US); William J. Shaw, Cambridge, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 64 days.

(21) Appl. No.: 12/379,252

(22) Filed: Feb. 17, 2009

(65) Prior Publication Data
US 2009/0216265 A1 Aug. 27, 2009

Related U.S. Application Data

(63) Continuation of application No. 10/230,672, filed on Aug. 29, 2002, now abandoned.

(51) Int. Cl.
*A61B 17/08* (2006.01)
(52) U.S. Cl.
USPC .......................................... 606/213; 606/153
(58) Field of Classification Search
USPC ......... 606/144, 151, 153, 213, 139, 205–209, 606/232
See application file for complete search history.

(56) References Cited

U.S. PATENT DOCUMENTS

| 4,006,747 | A | | 2/1977 | Kronenthal et al. |
| 5,091,205 | A | | 2/1992 | Fan |
| 5,217,484 | A | * | 6/1993 | Marks ........................... 606/200 |
| 5,702,421 | A | * | 12/1997 | Schneidt ....................... 606/213 |
| 5,733,294 | A | | 3/1998 | Forber et al. |
| 5,928,250 | A | * | 7/1999 | Koike et al. ................... 606/139 |
| 5,976,127 | A | | 11/1999 | Lax |

(Continued)

FOREIGN PATENT DOCUMENTS

| JP | 51-130091 | 11/1976 |
| JP | 06-510460 | 11/1994 |

(Continued)

OTHER PUBLICATIONS

Charles J. Lightdale, M.D., "Gastroesophageal Reflux Disease: New Endoscopic Treatments" *Digestive Disease Week 2001*, Atlanta, Ga.

(Continued)

*Primary Examiner* — Tuan V Nguyen
(74) *Attorney, Agent, or Firm* — Bookoff McAndrews, PLLC

(57) ABSTRACT

Surgical tissue fasteners and related deployment systems and methods are disclosed. A tissue fastener used to join multiple tissue layers includes a first member, a second member, and a connecting member connecting the first and second members. In some embodiments, the first and second members are configured to expand from a delivered state to a deployed state in which the fastener secures the tissue layers together. In other tissue fastener embodiments the connecting member has an elastic compressive spring force for applying a substantially constant force on the tissue layers for adjusting a length of the connecting member between the first and second members.

23 Claims, 30 Drawing Sheets

(56) References Cited

U.S. PATENT DOCUMENTS

| | | | |
|---|---|---|---|
| 6,080,182 A * | 6/2000 | Shaw et al. | 606/213 |
| 6,113,609 A * | 9/2000 | Adams | 606/139 |
| 6,174,322 B1 * | 1/2001 | Schneidt | 606/213 |
| 6,231,561 B1 | 5/2001 | Frazier et al. | |
| 6,326,025 B1 | 12/2001 | Sigler et al. | |
| 6,416,522 B1 * | 7/2002 | Strecker | 606/143 |
| 6,425,900 B1 | 7/2002 | Knodel et al. | |
| 6,491,714 B1 | 12/2002 | Bennett | |
| 6,736,828 B1 * | 5/2004 | Adams et al. | 606/213 |
| 7,160,314 B2 | 1/2007 | Sgro et al. | |
| 7,344,553 B2 * | 3/2008 | Opolski et al. | 606/207 |
| 2001/0010005 A1 | 7/2001 | Kammerer et al. | |
| 2001/0037130 A1 | 11/2001 | Adams | |
| 2002/0156344 A1 | 10/2002 | Pasricha et al. | |
| 2003/0220660 A1 | 11/2003 | Kortenbach et al. | |

FOREIGN PATENT DOCUMENTS

| | | |
|---|---|---|
| JP | 10-504738 | 5/1998 |
| JP | 2001-52292 | 11/2001 |
| JP | 2002-503500 | 2/2002 |
| WO | WO 93/08740 | 5/1993 |
| WO | WO 96/01591 | 1/1996 |
| WO | WO 99/23953 | 5/1999 |
| WO | WO 99/33402 | 7/1999 |
| WO | WO 00/78227 A1 | 12/2000 |
| WO | WO 01/35834 A1 | 5/2001 |
| WO | WO 01/95818 A1 | 12/2001 |
| WO | WO 02/17771 A2 | 3/2002 |
| WO | WO 02/28289 A1 | 4/2002 |
| WO | WO 02/30335 A2 | 4/2002 |
| WO | WO 02/41790 | 5/2002 |

OTHER PUBLICATIONS

R.J. Mason, T.R. De Meester, et al., "Per Oral Endoscopic Nissen Fundoplication: The Introduction of a New Era," *Program and Abstracts of Digestive Disease Week 2001*, Atlanta, Ga.

PCT Invitation to Pay Additional Fees (Form PCT/ISA/206) and Annex to Form PCT/ISA/206, entitled "Communication Relating to the Results of the Partial International Search," for PCT Application No. PCT/US 03/25818, mailed on Jan. 14, 2004.

* cited by examiner

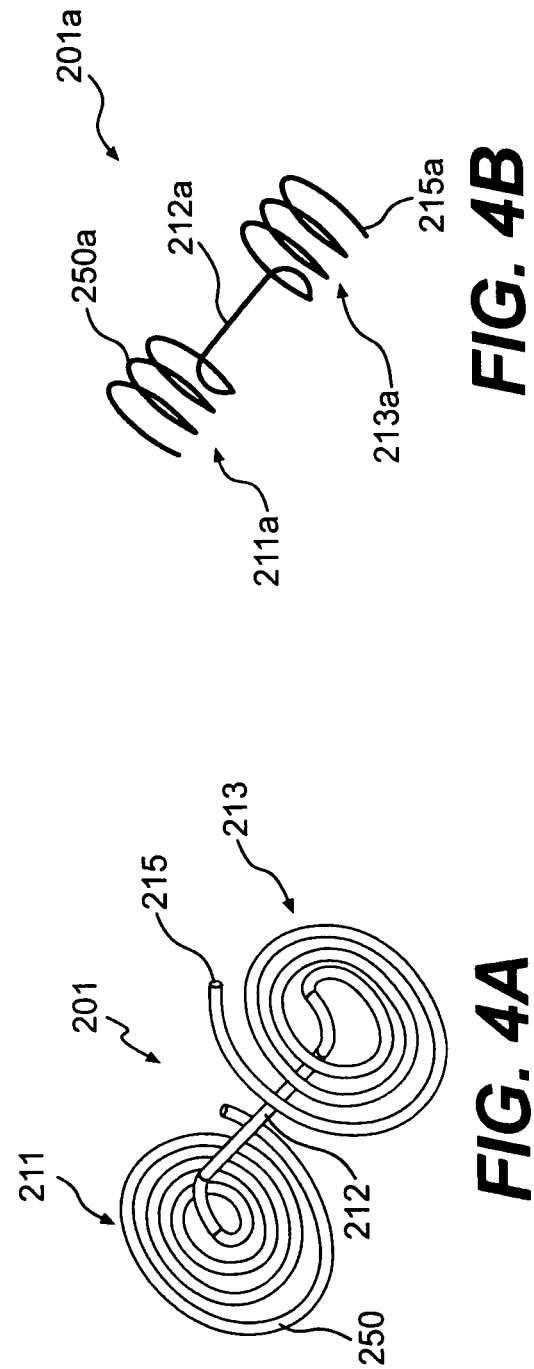

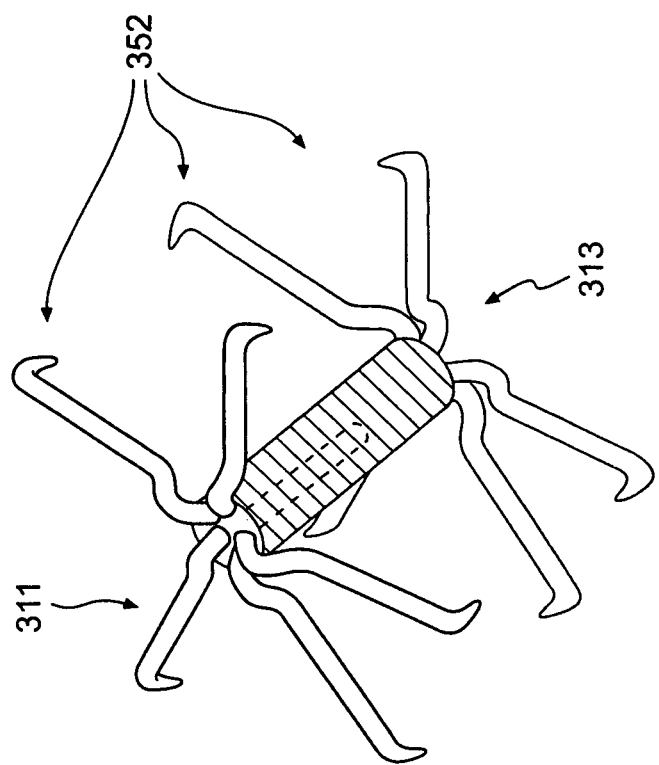
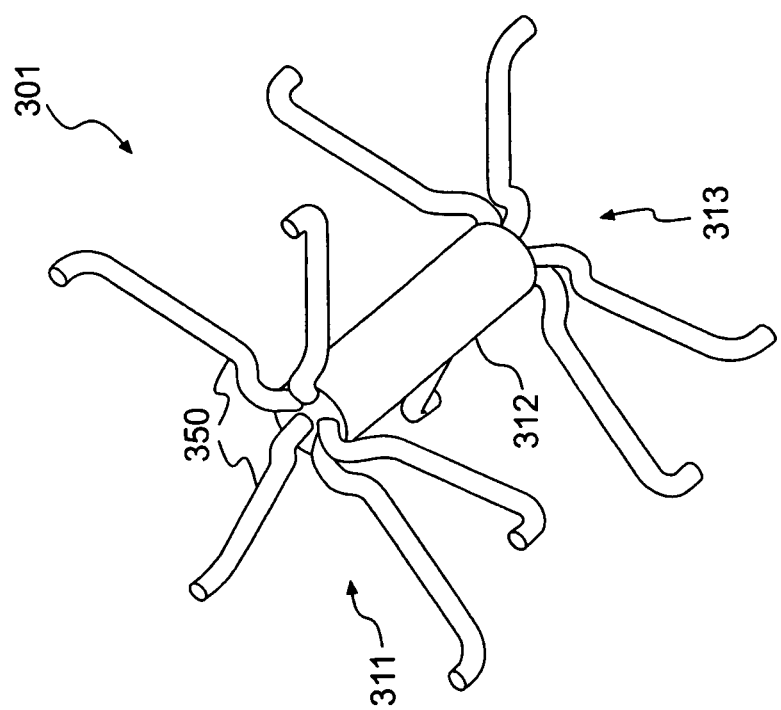

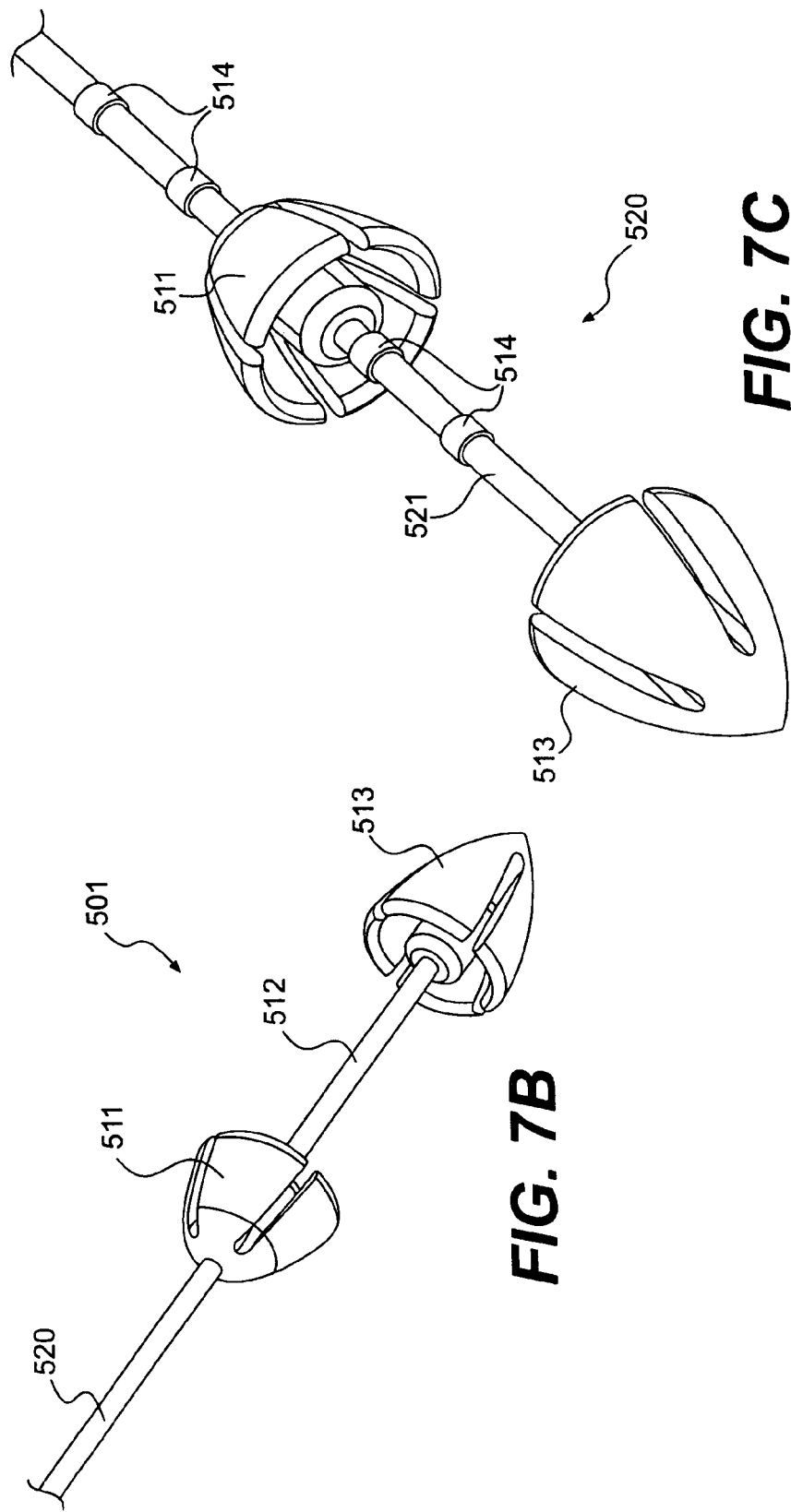

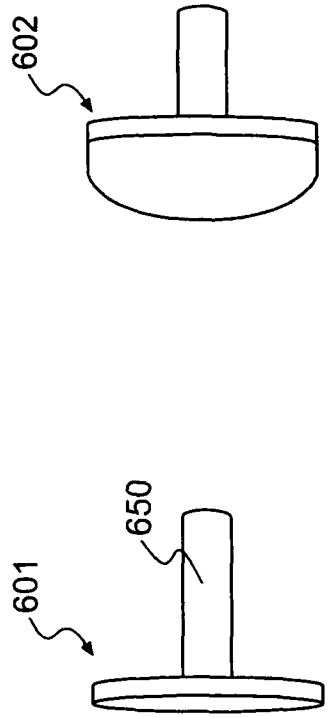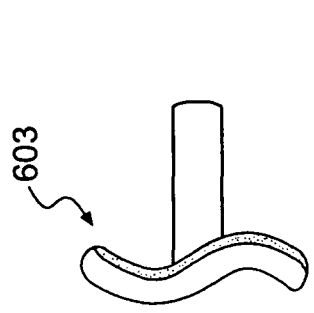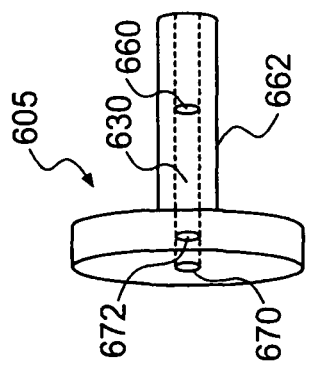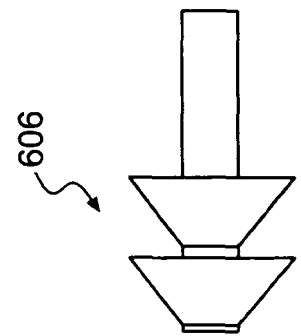
FIG. 8A   FIG. 8B   FIG. 8C
FIG. 8D   FIG. 8E   FIG. 8F

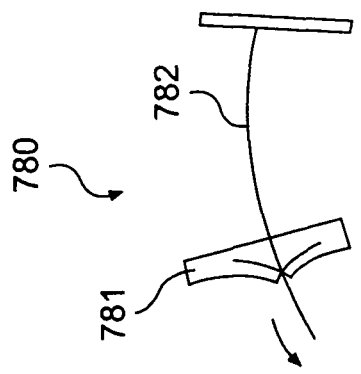
FIG. 10G
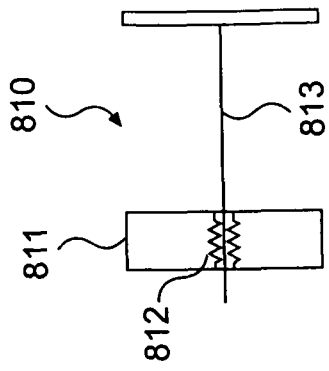
FIG. 10J
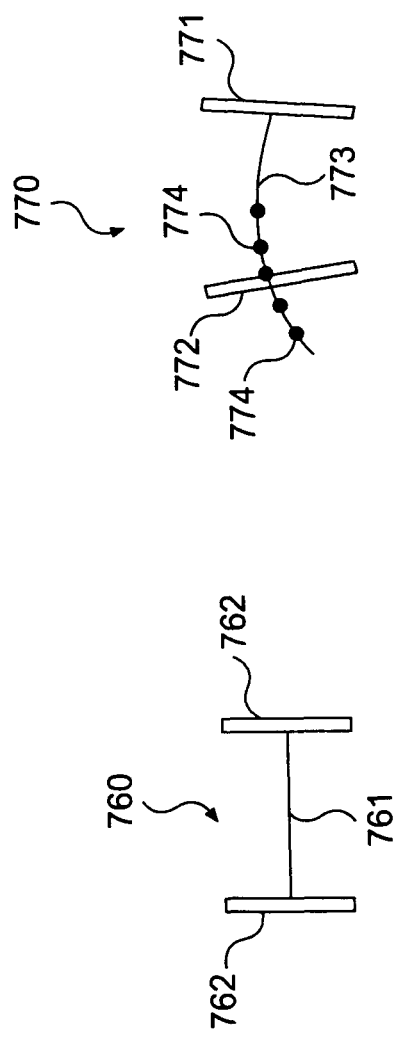
FIG. 10F
FIG. 10E
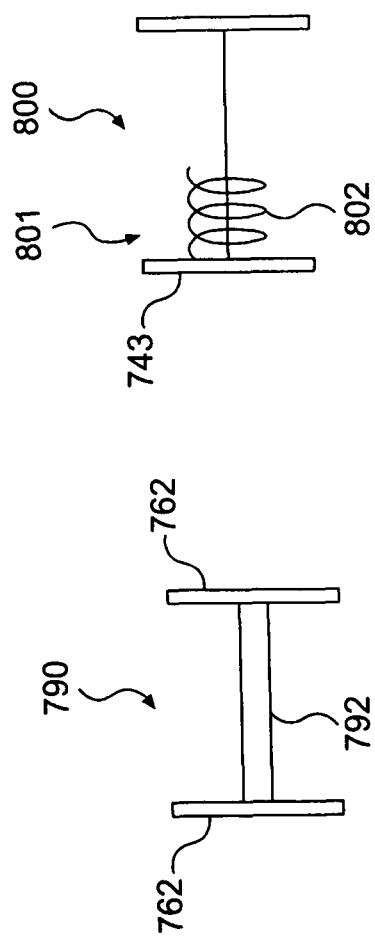
FIG. 10I
FIG. 10H

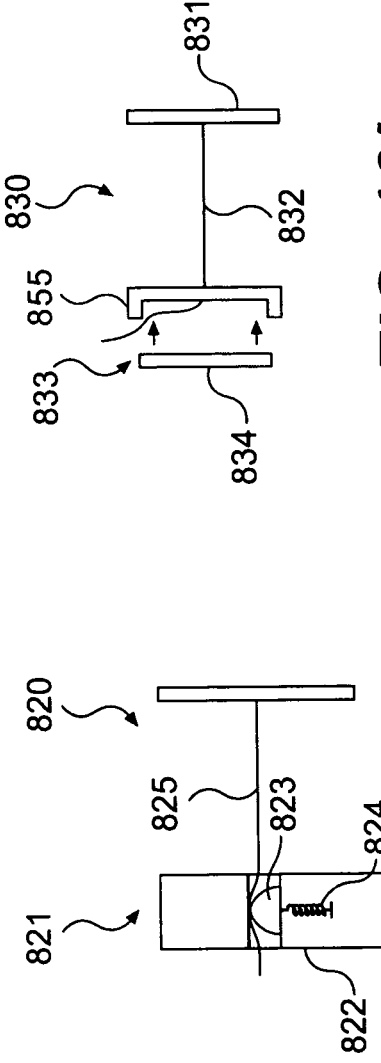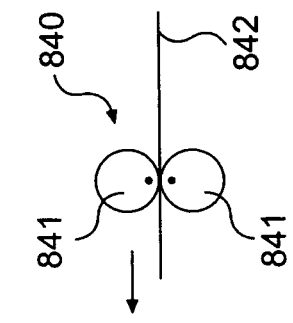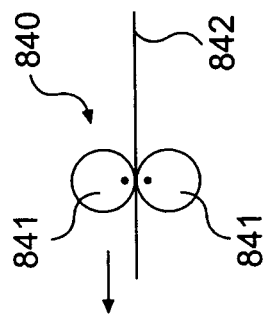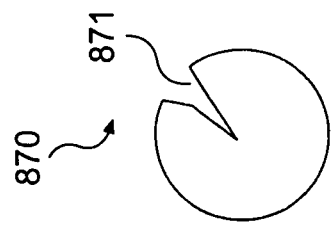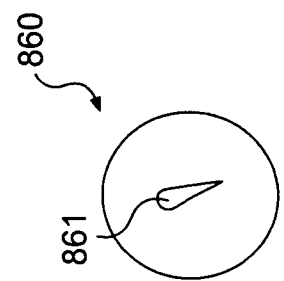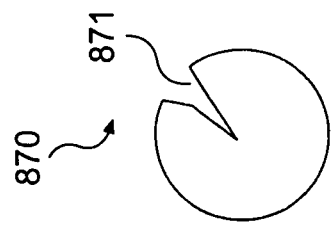

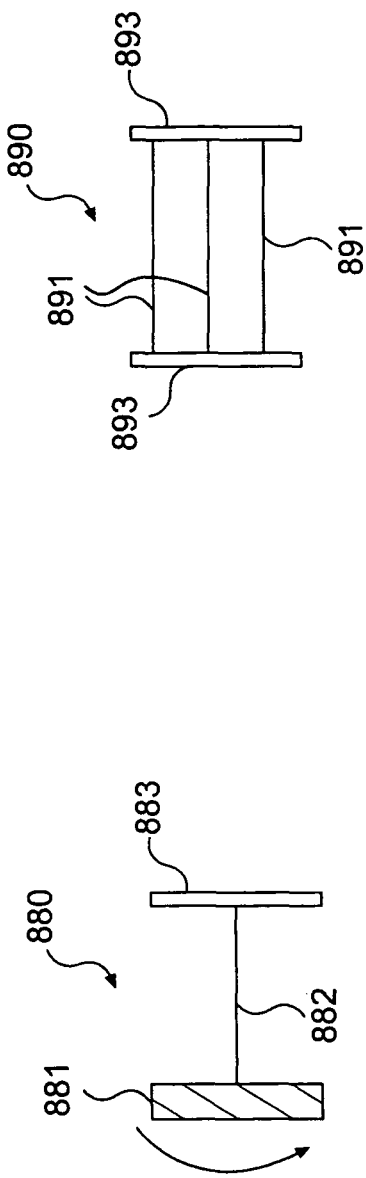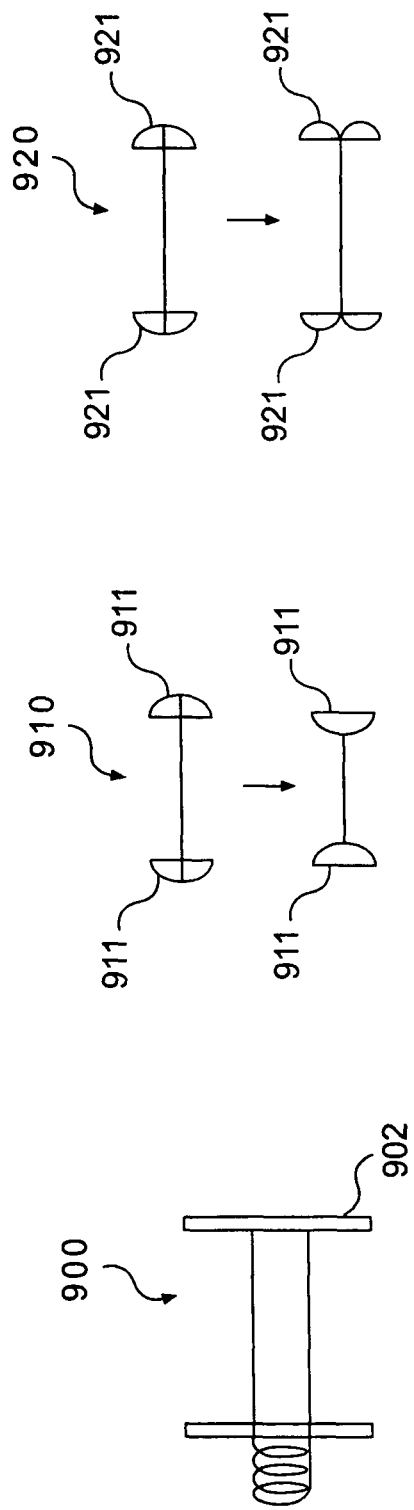

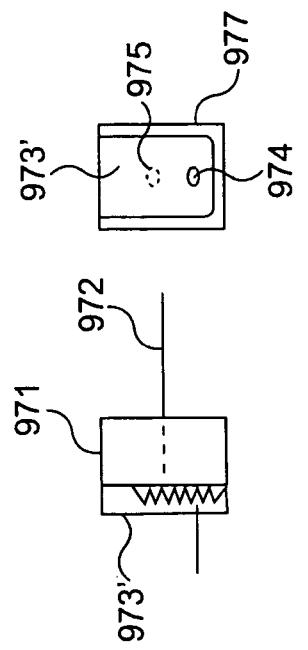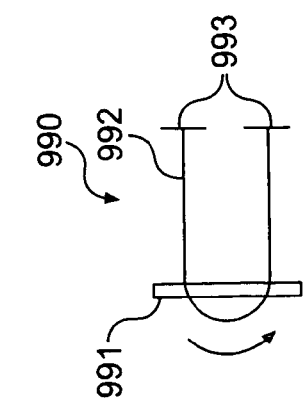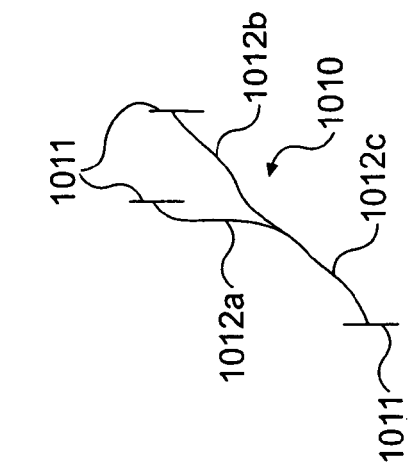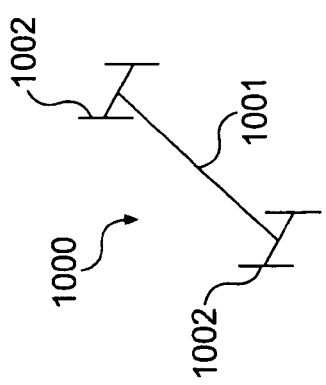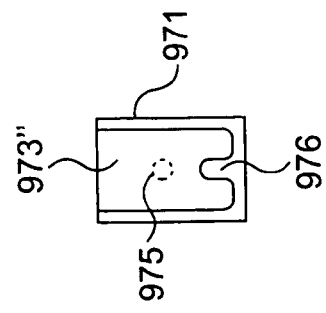
FIG. 10DD
FIG. 10GG
FIG. 10CC
FIG. 10FF
FIG. 10BB
FIG. 10EE

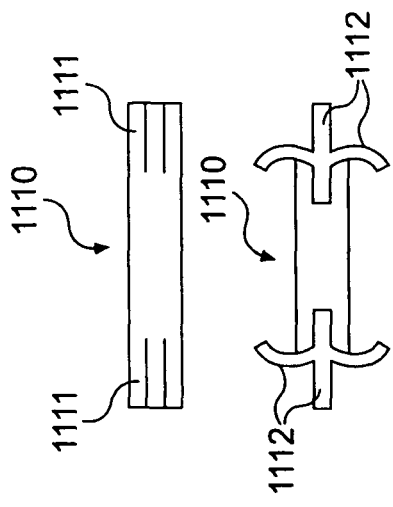
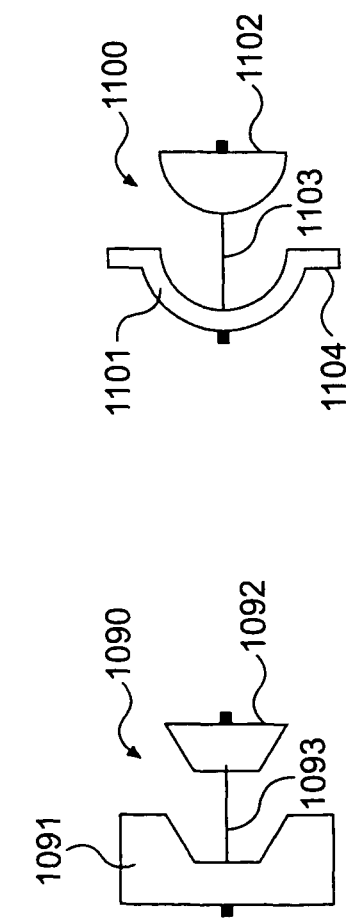
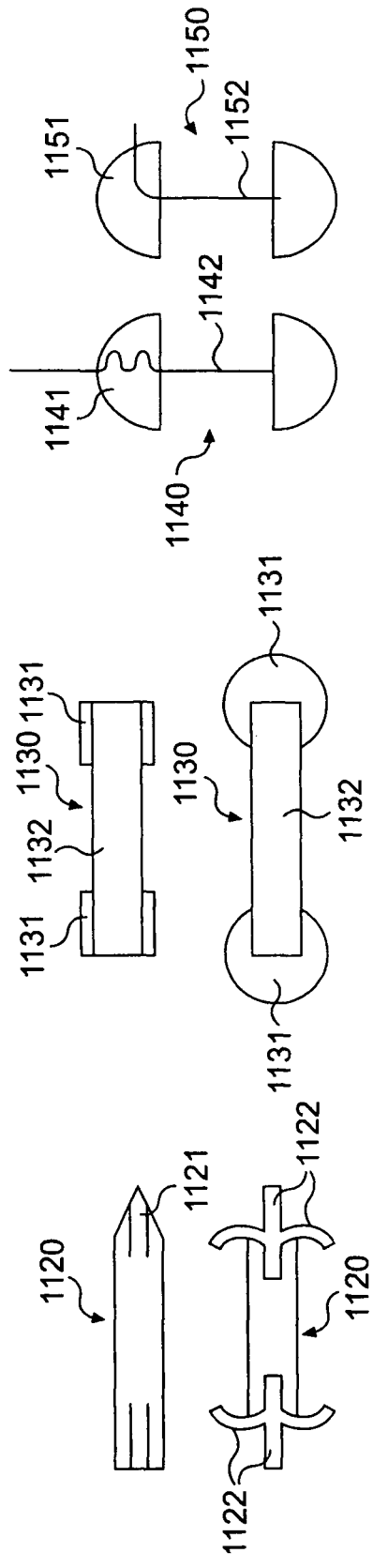

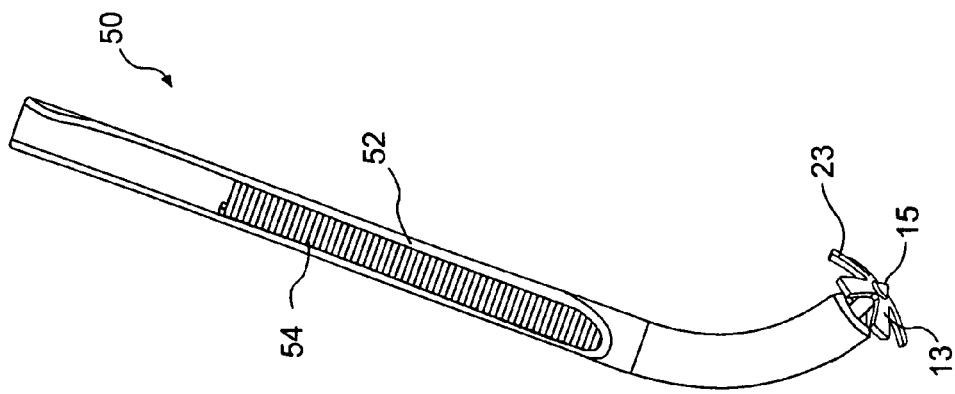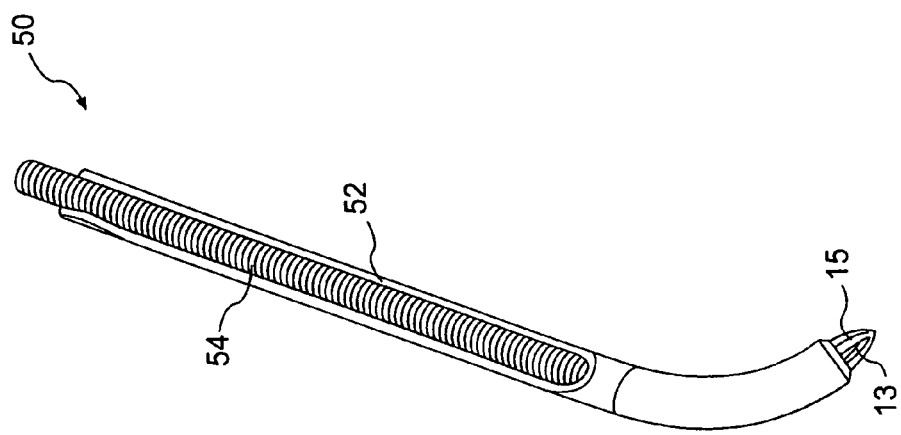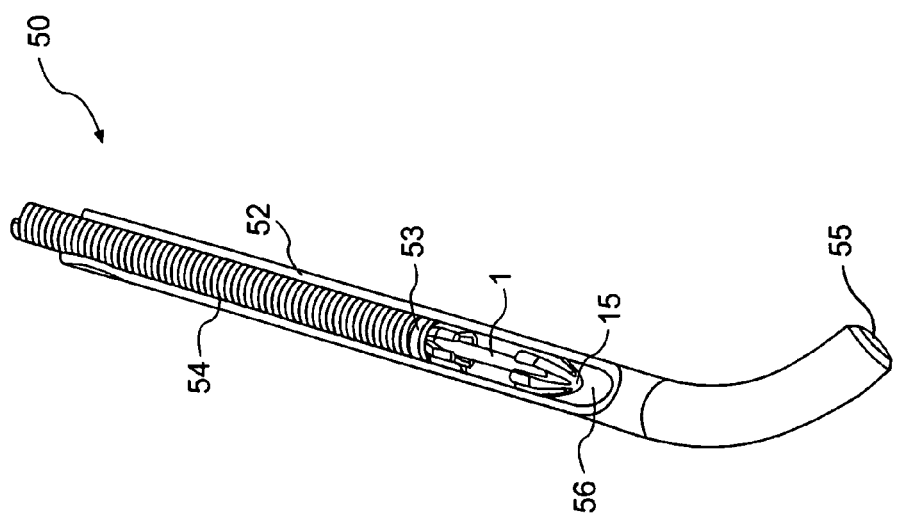

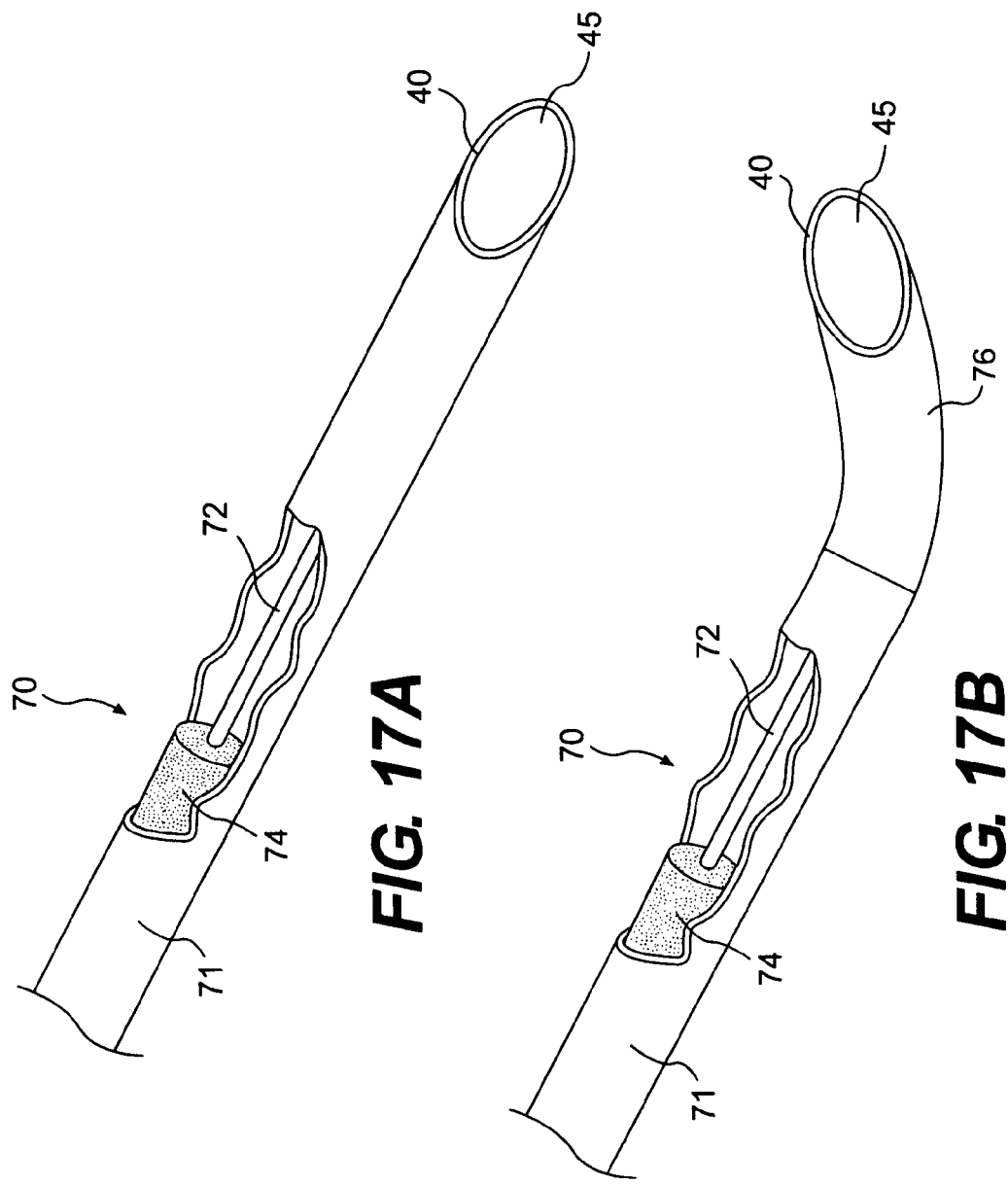

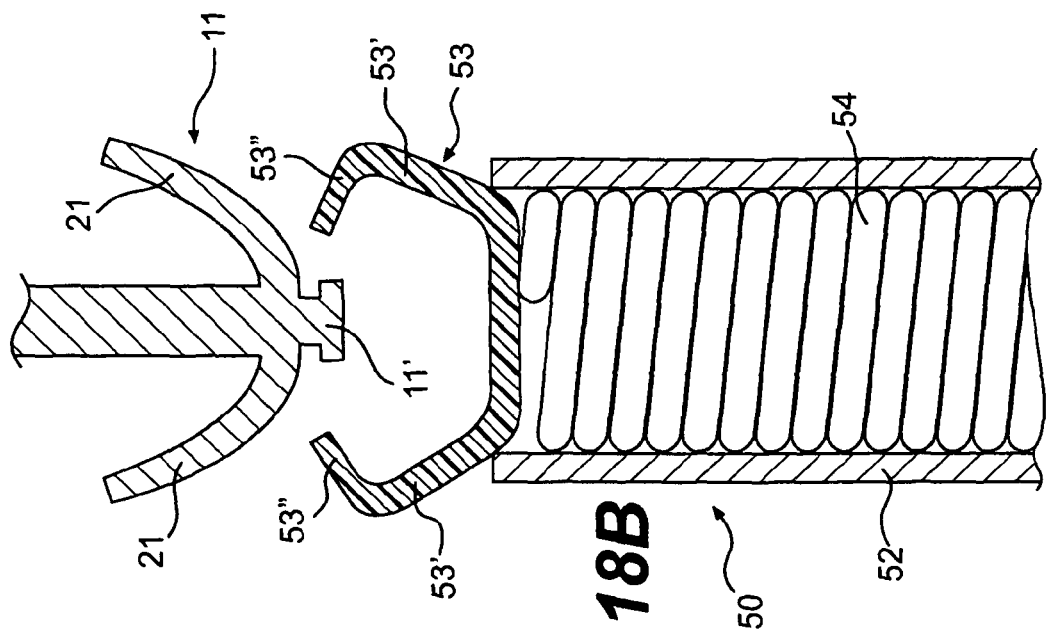
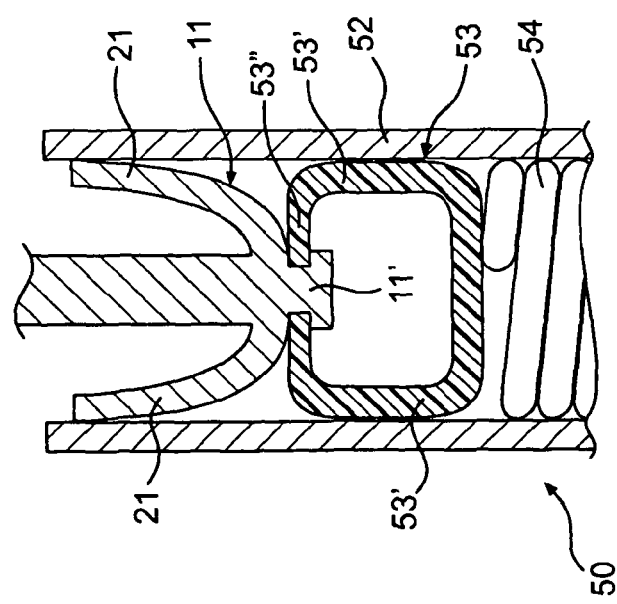

TISSUE FASTENERS AND RELATED DEPLOYMENT SYSTEMS AND METHODS

CROSS-REFERENCE TO RELATED APPLICATIONS

This application is a continuation of application Ser. No. 10/230,672, filed Aug. 29, 2002, now abandoned, the contents of which are relied upon and incorporated herein by reference. This application relates to commonly assigned U.S. application Ser. No. 10/230,682, of Robert Devries et al., filed on Aug. 29, 2002, now U.S. Pat. No. 7,083,630, and entitled "Devices and Methods for Fastening Tissue Layers." The complete disclosure of that application is incorporated by reference herein.

DESCRIPTION OF THE INVENTION

1. Field of the Invention

The present invention relates to surgical tissue fasteners and related deployment systems and methods for delivering the tissue fasteners. In particular, the present invention relates to tissue fasteners used in, for example, a fundoplication procedure for treatment of Gastroesophageal Reflux Disease (GERD).

2. Background of the Invention

Gastroesophageal reflux occurs when stomach acid enters the esophagus. This reflux of acid into the esophagus occurs naturally in healthy individuals, but also may become a pathological condition in others. Effects from gastroesophageal reflux range from mild to severe. Mild effects include heartburn, a burning sensation experienced behind the breastbone. More severe effects include a variety of complications, such as esophageal erosion, esophageal ulcers, esophageal stricture, abnormal epithelium (e.g., Barrett's esophagus), and/or pulmonary aspiration. These various clinical conditions and changes in tissue structure that result from reflux of stomach acid into the esophagus are referred to generally as Gastroesophageal Reflux Disease (GERD).

Many mechanisms contribute to prevent gastroesophageal reflux in healthy individuals. One such mechanism is the functioning of the lower esophageal sphincter (LES). With reference to FIG. 1, the LES 2 is a ring of smooth muscle and increased annular thickness existing in approximately the last four centimeters of the esophagus. In its resting state, the LES creates a region of high pressure (approximately 15-30 mm Hg above intragastric pressure) at the opening of the esophagus 3 into the stomach 7. This pressure essentially closes the esophagus 3 so that contents of the stomach cannot pass back into the esophagus 3. The LES 2 opens in response to swallowing and peristaltic motion in the esophagus 3, allowing food to pass into the stomach. After opening, however, a properly functioning LES 2 should return to the resting, or closed state. Transient relaxations of the LES 2 do occur in healthy individuals, typically resulting in occasional bouts of heartburn.

The physical interaction occurring between the gastric fundus 5 and the esophagus 3 also prevents gastroesophageal reflux. The gastric fundus 5 is a lobe of the stomach situated at the top of the stomach 7 distal to the esophagus 3. In asymptomatic individuals, the fundus 5 presses against the opening of the esophagus 3 when the stomach 7 is full of food and/or gas. This effectively closes off the esophageal opening to the stomach 7 and helps to prevent acid reflux back into the esophagus 3. More specifically, as the food bolus is immersed in gastric acid, it releases gas which causes the fundus 5 of the stomach 7 to expand and thereby exert pressure on the distal esophagus 3 causing it to collapse. The collapse of the esophagus lumen reduces the space for the stomach acid to splash past the closed esophagus lumen and thereby protect the proximal esophagus from its destructive contact.

In individuals with GERD, the LES 2 functions abnormally, either due to an increase in transient LES relaxations, decreased muscle tone of the LES 2 during resting, or an inability of the esophageal tissue to resist injury or repair itself after injury. These conditions often are exacerbated by overeating, intake of caffeine, chocolate or fatty foods, smoking, and/or hiatal hernia. Avoiding these exacerbating mechanisms helps curb the negative side effects associated with GERD, but does not change the underlying disease mechanism.

A surgical procedure, known generally as fundoplication, has been developed to prevent acid reflux in patients whose normal LES functioning has been impaired, either as a result of GERD or other adverse effects. This procedure involves bringing the fundus wall 6 into closer proximity of the esophageal wall 4 to help close off the esophageal opening into the stomach 7. Traditionally, this procedure has been performed as an open surgery, but also has been performed laparoscopically.

As with any surgery, the attendant risks are great. Due to relatively large incisions necessary in the performance of open surgery, relatively large amount of blood is lost, the risk of infection increases, and the potential for postoperative hernias is high. Further, the relatively large incisions necessary in the performance of open surgery require extended recovery times for the incision to heal.

A laparoscopic procedure may involve performing laparotomies for trocar ports (penetrations of the abdominal wall), percutaneous endoscopic gastronomies (incisions through the skin into the stomach), and the installation of ports through which, for example, a stapler, an endoscope, and an esophageal manipulator (invagination device) are inserted. Under view of the endoscope, the esophageal manipulator is used to pull the interior of the esophagus 3 into the stomach 7. When the esophagus is in position, with the fundus 5 of the stomach plicated, the stapler is moved into position around the lower end of the esophagus and the plicated fundus is stapled to the esophagus 3. The process may be repeated at different axial and rotary positions until the desired fundoplication is achieved. This procedure is still relatively invasive requiring incisions through the stomach, which has a risk of infection. The location of the incision in the abdominal wall presents a risk of other negative effects, such as sepsis, which can be caused by leakage of septic fluid contained in the stomach.

SUMMARY OF THE INVENTION

Therefore, one embodiment of the present invention provides less invasive devices and methods for performing the fundoplication procedure. This is achieved by utilizing tissue fasteners and related deployment systems which can be endoluminally delivered through the esophagus 3, thereby eliminating the need for highly invasive, physiologically insulting surgical procedures.

To attain the advantages and in accordance with the purpose of the invention, as embedded and broadly described herein, one aspect of the invention provides a tissue fastener used to join multiple tissue layers. The tissue fastener includes a proximal member configured to expand from a delivered state to a deployed state, a distal member configured to expand from a delivered state to a deployed state, and a connecting member connecting the proximal member to the distal member. In the deployed state, the proximal member and the distal member secure the multiple tissue layers together.

Another aspect of the invention provides a tissue fastener used to join multiple tissue layers that includes a first member, a second member, a connecting member connecting the first member to the second member, and means for applying a substantially constant force on the tissue layers. In some embodiments, the applying means may be compressible.

Another aspect of the invention provides a tissue fastener used to join multiple tissue layers that includes a first member, a second member, a connecting member connecting the first member to the second member, and means for adjusting a length of the connecting member between the first and second members. In some embodiments, the adjusting means may include structure associated with the first member for releasably securing the connecting member to the first member. That structure may be configured to restrict passage of the connecting member in a direction through the first member.

Another aspect of the present invention is to provide a delivery system configured for deployment of an expandable tissue fastener. The system includes a flexible tube configured to accommodate a tissue fastener in a contracted state, a pusher for guiding the tissue fastener along a lumen of the tube, and a grasper coupled to a distal end of the pusher and having means to grasp the tissue fastener.

In yet another aspect of the present invention, a method of attaching a first layer of tissue to a second layer of tissue includes providing an expandable tissue fastener in a contracted state in a device, the tissue fastener having a proximal member and a distal member, inserting the device into a body passage leading to the first tissue wall, placing the device proximate a location on the first tissue layer, passing the device through the first and second tissue layers, advancing the tissue fastener toward an opening of the device, such that the distal member is completely protruded out of the device and expanded against the second tissue layer, and withdrawing the device and releasing the tissue fastener, such that the proximal member is expanded against the first tissue layer.

The present invention is depicted in this disclosure and is particularly suitable in the treatment of GERD, e.g., a fundoplication procedure. However, the tissue fasteners and related deployment methods and systems of the present invention can be used to treat any of a number of different disease conditions, and can be used for fastening any desired body tissues.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate several embodiments of the invention and together with the description, serve to explain the principles of the invention.

In the drawings:

FIGS. 3-7C are perspective views of various tissue fasteners according to various embodiments of the present invention;

FIGS. 11A-C are perspective views of an endoluminal deployment system, illustrating various operational stages of the system for deployment of a tissue fastener, according to an embodiment of the present invention;

FIG. 17A is a perspective view of a deployment system, with a straight distal tip, according to another embodiment of the present invention;

FIG. 17B is a perspective view of a deployment system, with a curved distal tip, according to still another embodiment of the present invention; and FIGS. 18A and 18B are views of a deployment system respectively holding and releasing a tissue fastener member.

DESCRIPTION OF THE EMBODIMENTS

Reference will now be made in detail to the exemplary embodiments of the invention, examples of which are illustrated in the accompanying drawings. Wherever possible, the same reference numbers will be used throughout the drawings to refer to the same or like parts.

A newly developed form of fundoplication, referred to as endoscopic fundoplication, is an endoluminal procedure in which the fundus wall 6 is folded back onto the esophagus wall 4. The tissue fold formed between the esophagus 3 and the fundus 5 then is secured. Endoscopic fundoplication is intended to be performed as an endoluminal procedure in which insertion of required medical instruments occurs through the esophagus 3. Such a procedure has the benefits of being less invasive, quicker, and less expensive as compared to previous techniques.

Figure 1:
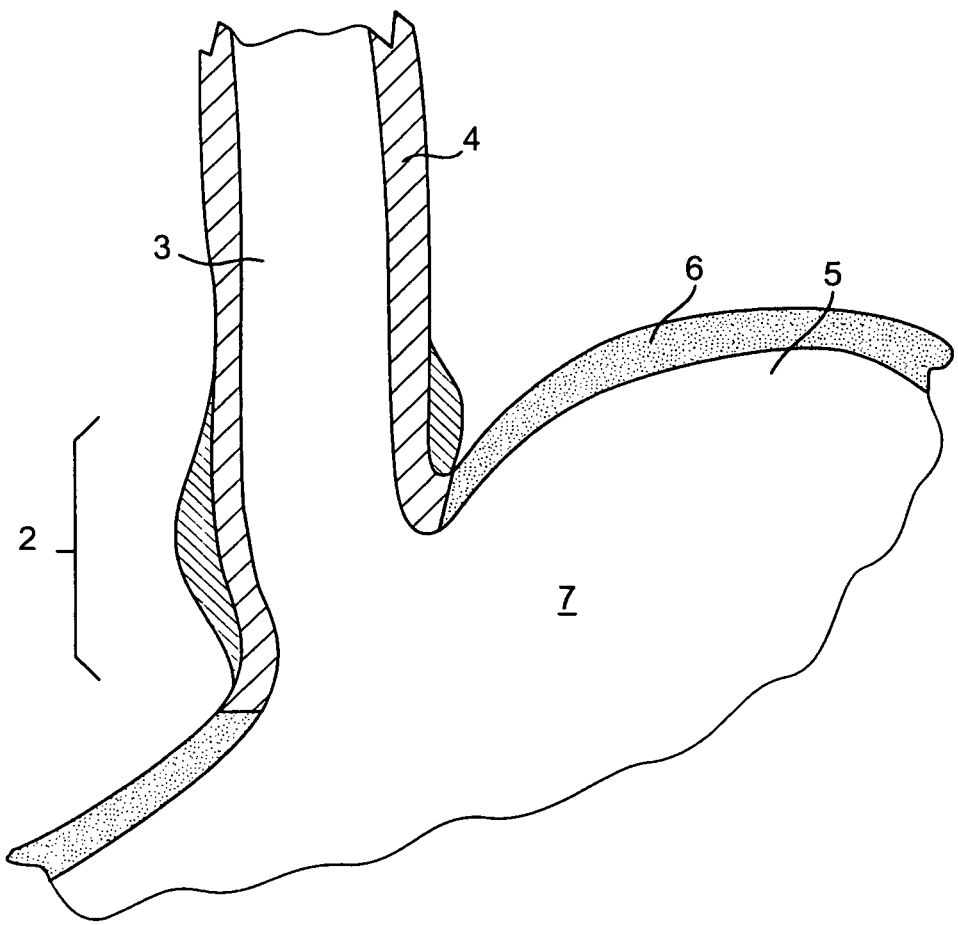
FIG. 1 is a cross-sectional view of the gastrointestinal tract in the region of the lower esophageal sphincter (LES) and the fundus of the stomach.
Figure 2A:
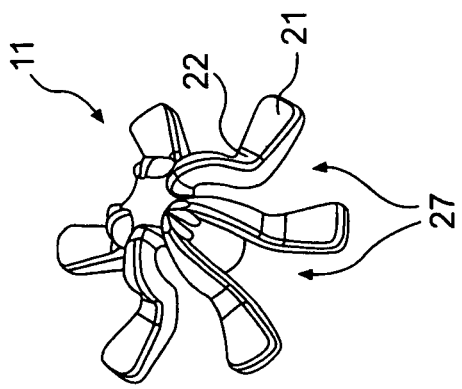
FIG. 2A is a perspective view of a proximal fastening member of the tissue fastener of FIG. 2, showing the proximal fastening member in a deployed state according to an embodiment of the present invention.
Figure 2B:
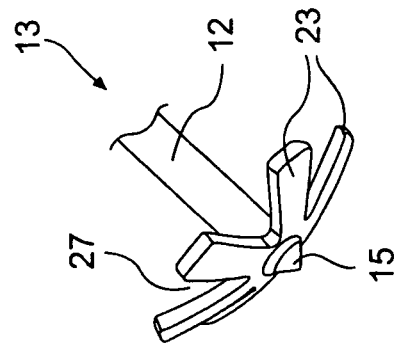
FIG. 2B is a perspective view of a distal fastening member of the tissue fastener of FIG. 2 in a deployed state, according to an embodiment of the present invention.
Figure 2:
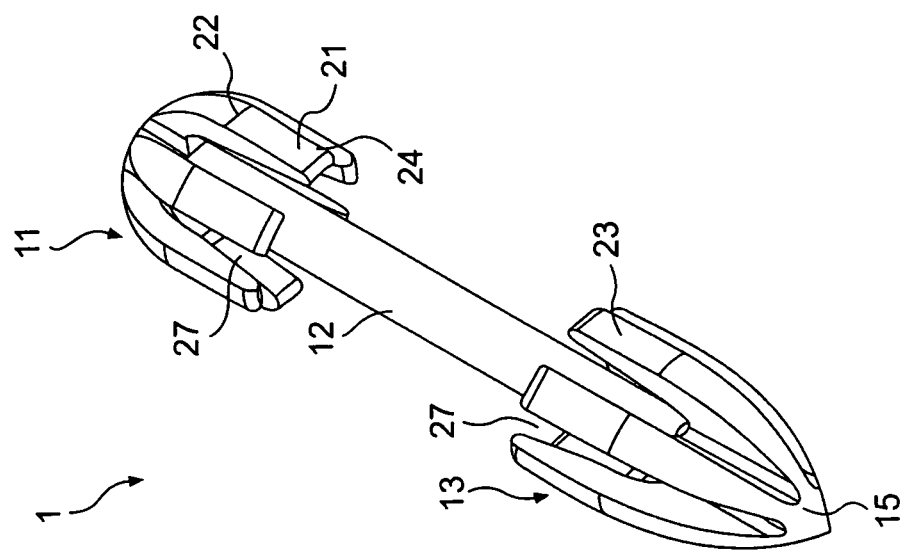
FIG. 2 is a perspective view of a tissue fastener, prior to deployment into a body, according to an embodiment of the present invention.

FIG. 2 shows an exemplary embodiment of a tissue fastener 1 for use in a fundoplication procedure. The tissue fastener 1 has a distal fastening member 13, a proximal fastening member 11, and a connecting member 12 connecting the distal fastening member 13 and the proximal fastening member 11 to each other. The distal fastening member 13, the proximal fastening member 11, and the connecting member 12 are formed as an integrated unit or two or more components pieced together. The distal fastening member 13 includes a plurality of anchor hooks or legs 23, and the proximal fastening member 11 includes a plurality of anchor hooks or legs 21. The plurality of anchor legs 21, 23 are constructed to expand from a contracted state to an expanded state. When the legs are in the contracted state, as shown in FIG. 2, the tissue fastener 1 is low in profile and can be loaded into a narrow lumen of an endoluminal deployment system for deployment. Once the deployment system is positioned into a desired location within a body, the plurality of anchor legs 21, 23 are expanded outwardly to fasten multiple tissue layers together between the distal and proximal fastening members 13, 11, thereby enhancing the tissue connection.

In this particular embodiment shown in FIG. 2, each of the distal and proximal fastening members 11, 13 is provided with a total of six anchor legs 21, 23, that are equally spaced apart. However, it should be recognized that the fastening members 11, 13 can be provided with more or less number of legs 21, 23 with different desired spacing therebetween.

Preferably, the leading edge of the distal fastening member 13 forms a sharp point or edge 15 to assist with penetrating through the tissue layers. The sharp edge 15 may be a trocarlike cutting edge to perform the perforation of the layers itself. It should also be recognized that forming such a sharp cutting edge 15 may not be necessary if an endoluminal deployment system includes a cutting edge 40 on its distal tip, as shown in FIGS. 17A-B to be described herein.

FIGS. 2A and 2B show the expanded state of the proximal and distal fastening members 11, 13, respectively in an installed state. When the distal fastening member 13 is freed from a restraining means of an endoluminal deployment system, the anchor legs 23 of the distal fastening member 13 expand outwardly to form an umbrella-shaped fastening member. Sharp edge or tip 15 may be removed or made of a dissolvable, biodegradable material. Similarly, when the proximal fastening member 11 is freed from a restraining means of an endoluminal deployment system, the anchor legs 21 of the proximal fastening member 11 expand outwardly to form a fastening member. Each of the anchor legs 21 of the proximal fastening member 11 may include one or more bending portions 22 at a location along the length of the leg 21, such that the distal portion 24 of the leg 21 extends outwardly with respect to the bending portion 22. The bending portion 22 is a relatively flexible portion of an otherwise substantially rigid leg 21. The bending portion 22 may be facilitated by removal of material or change in geometry along the leg 21. The leg 21 may further comprise a variable stiffness along the leg 21. For example, the bending portion 22 may consist of a lower stiffness material to facilitate the bending.

FIGS. 3 through 7 are perspective views of various tissue fasteners in expanded states according to other embodiments of the invention. In an embodiment shown in FIG. 3, the tissue fastener 101 is formed of at least two elongate members 150, such as wires or rods, interconnected in the mid-portion by a connecting member 112. The interconnection may be made through any suitable method, such as welding, brazing, molding, a locking mechanism, etc., or members may be manufactured as an integral piece. In a contracted state, each member 150 is preferably substantially straight to promote easier insertion through the esophagus and deployment. In an expanded state, shown in the figure, each member 150 bends outwardly, substantially perpendicular to the connecting member 112, to form the distal and proximal fastening members 113, 111. The ends of the proximal fastening member 111 could be rounded or otherwise protected to reduce trauma when in contact with tissue. Similar to the embodiment shown in FIG. 2, the leading edge of each member 150 may form a sharp cutting edge 115 to assist with perforating layers of tissues.

Figure 3A:
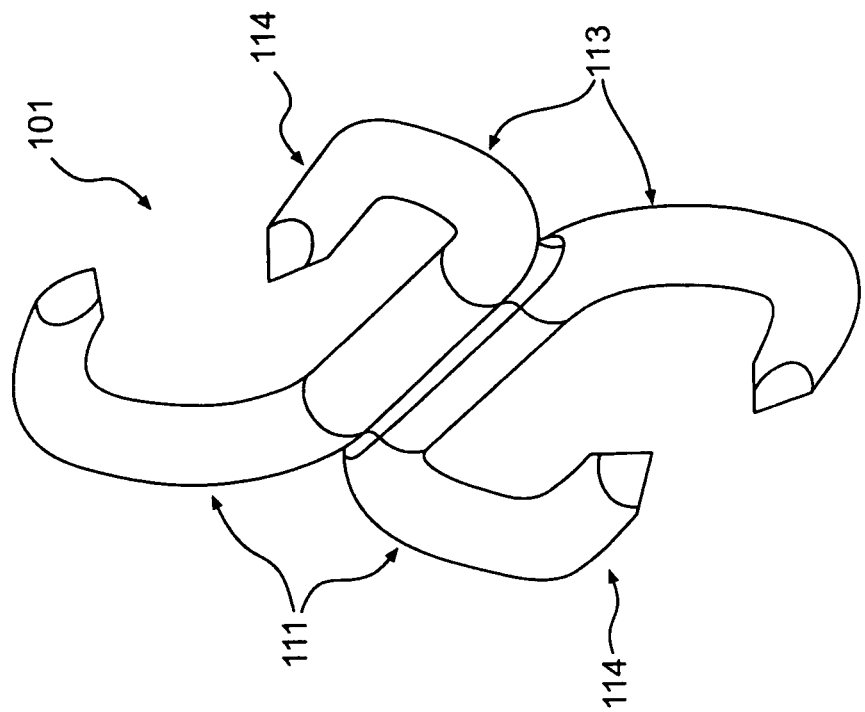
Figure 3:
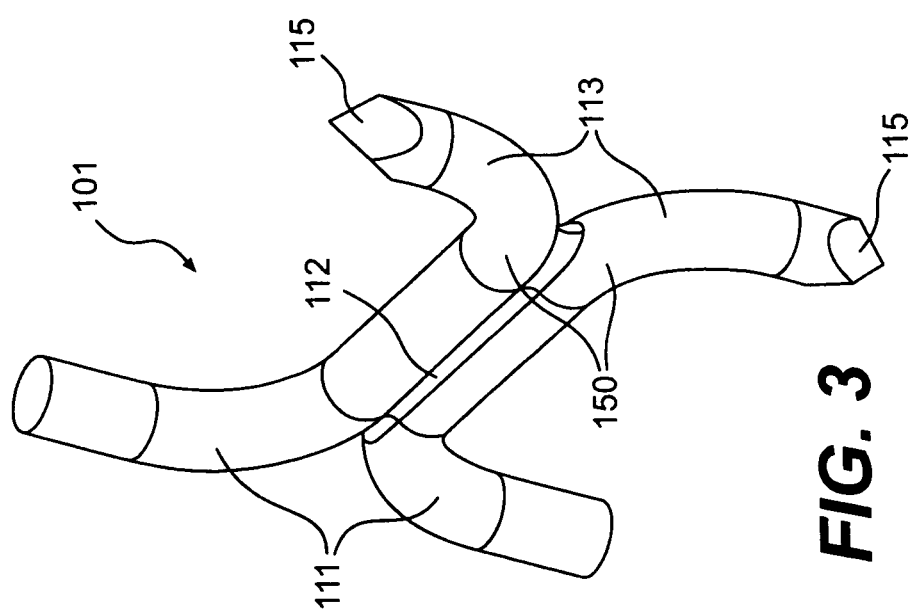

FIG. 3A illustrates a further embodiment of the fastener of FIG. 3 wherein the distal and proximal ends of the fastener 101 turn inwards upon deployment through tissue layers. These inward turns, or hooks 114, would contact tissue and prevent migration of fastener 101.

According to another embodiment shown in FIG. 4A, the tissue fastener 201 is comprised of a single wire 250 or rod. Similar to the tissue fastener 101 of FIG. 3, the wire 250 preferably forms a substantially straight wire in a contracted state. In an expanded state, shown in the figure, the wire 250 forms spiral-shaped distal and proximal fastening members 213, 211 at both ends of the wire 250, that are substantially perpendicular to the connecting member 212. The wire 250a may also form a spring-shaped fastening member 211a, 213a at both ends of the wire 250a, as shown in FIG. 4B. In that case, the spring-shaped fastening members 211a, 213a may be substantially parallel to the connecting member 212a. The leading edge of the wire 250 may form a sharp cutting edge 215 to assist with perforating layers of tissues. As a modification and alternative to fastener 201, a wire fastener may be delivered in a straight configuration and forms into a coil that may be screwed into the tissue layers. As described below, a suitable material for such fasteners is nitinol.

The tissue fastener 301 shown in FIG. 5A is comprised of multiple wires integrally attached to a connecting member 312. In a contracted state, each wire 350 preferably forms a substantially straight wire and, in an expanded state, shown in the figure, the wires 350 expand outwardly to form spider-shaped distal and proximal fastening members 313, 311. While the leading edges of the wires 350 may form sharp cutting edges to assist with perforating the tissue layers, it may be most beneficial to use an endoluminal deployment system with a trocar-like cutting edge, such as the device shown in FIGS. 17A-B, or other perforating instrument to form an opening through the tissue layers prior to the deployment of the tissue fastener 301. In, an alternative embodiment to FIG. 5A, and as shown in FIG. 5B, the fastening members 311,313 may include inwardly bent hooks 352 at each end portion of the wires 350 to prevent migration of the fastener once deployed onto the tissue layers.

Figure 6:
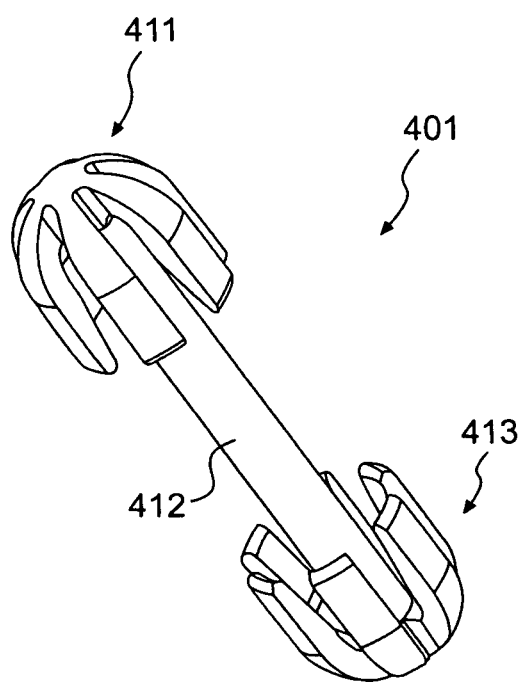

As shown in FIG. 6, the tissue fastener 401 has a similar configuration as the tissue fastener 1 shown in FIG. 2, except that the distal and proximal fastening member 413, 411 have the same configuration, much like the fastening member 11 shown in FIG. 2. In particular, the distal fastening member 413 does not include a sharp pointed edge. For this tissue fastener 401, an endoluminal deployment system with a trocar-like cutting edge (e.g., a device shown in FIGS. 17A-B) can be utilized.

Figure 7A:
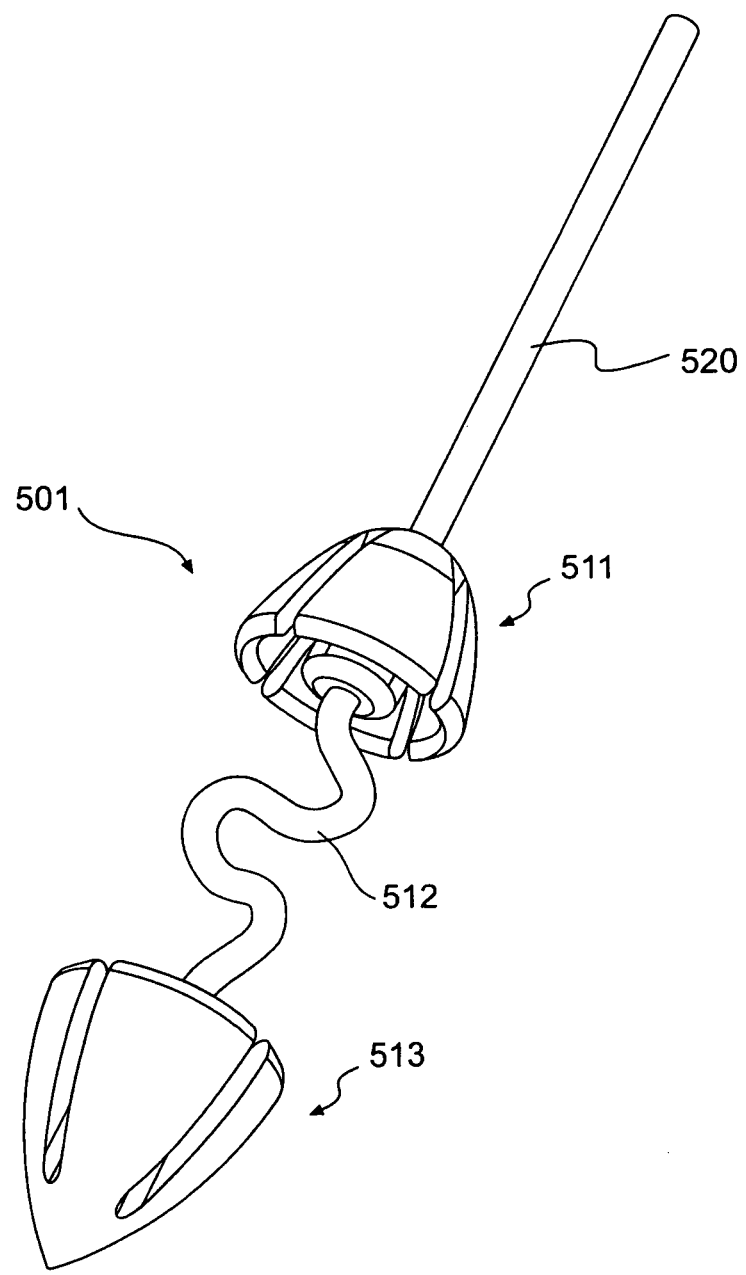

FIG. 7A shows a tissue fastener 501, also similar to the tissue fastener 1 shown in FIG. 2 in certain respects. The tissue fastener 501 has a distal fastening member 513, a proximal fastening member 511, and an adjustable connecting member 512. The distal fastening member 513 and the proximal fastening member 511 function in a similar manner as these corresponding structures of the tissue fastener 1 shown in FIG. 2. In the embodiment shown in FIG. 7A, the tissue fastener 501 includes an adjustable connecting member 512. Once fastener 501 has been placed through the tissue layers to be connected, tail 520 of fastener 501 is pulled taut as illustrated in FIG. 7B and fastening member 511 is advanced forward. This action creates a compressive force on the tissues between the fastening members 511 and 513. Alternatively, the connecting member 512 has an elastic compressive spring force which exerts pulling force between the distal and proximal fastening members 513, 511 so that the fastening of the multiple tissue layers is enhanced.

Figure 7D:
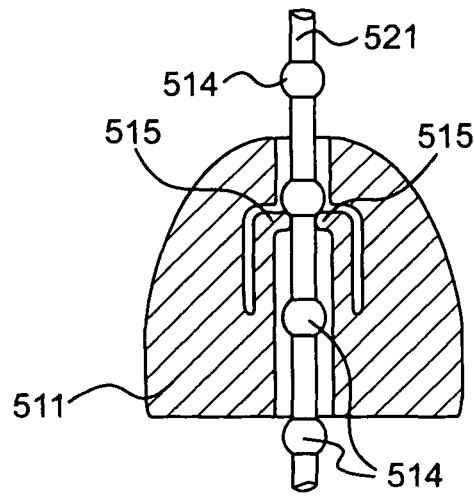
FIGS. 7D-7F are cross-sectional views of tissue fastener members according to various embodiments of the present invention.
Figure 7E:
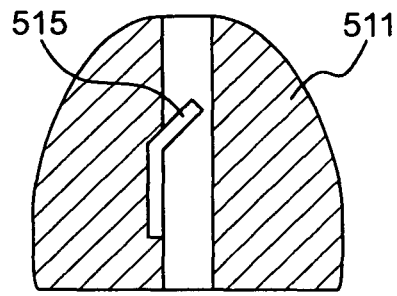
Figure 7F:
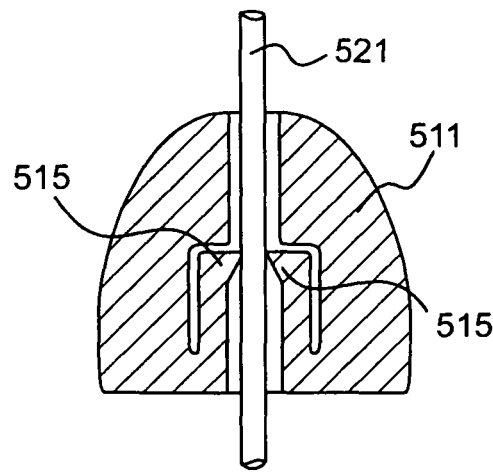

The elastic compressive force may be further combined with the adjustable system as described. FIGS. 7C through 7F illustrate adjustable fasteners of the present invention. FIG. 7C illustrates a fastener 520 have fastening members 513 and 511 and an adjustable connecting member 521. Member 521 further includes bumps (or notches) 514 which allow fastening member 511 to ratchet forward as either member 511 is advanced or connecting member 521 is pulled taut to connect tissue layers. FIGS. 7D through 7F illustrate cross-sectional views of two ratcheting systems as described. In FIG. 7D, the ratcheting action is created by virtue of flexible tabs 515 located inside fastening member 511. FIGS. 7E and 7F illustrate friction based or infinite ratcheting systems wherein the interference fit of a single tab 515 of FIG. 7E or of multiple tabs 515 of FIG. 7F serve to keep connecting member 521 from slipping once fastening member 511 is advanced forward onto tissue or connecting member 521 is pulled taut. If connecting member 521 is at least partially elastic, the fastener may be self adjusting once in place or the force within the fastener upon the tissues may be controlled.

Figure 8I:
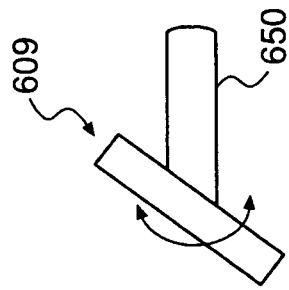
FIGS. 8A-8R are perspective views of various designs of tissue fastening members according to additional embodiments of the present invention.
Figure 8H:
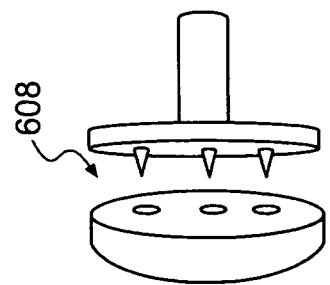
Figure 8G:
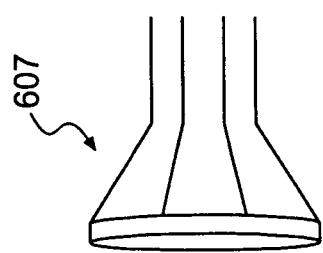
Figure 8L:
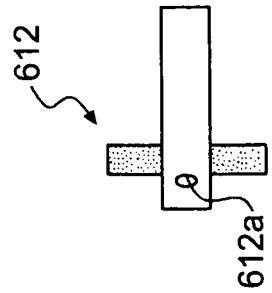
Figure 8K:
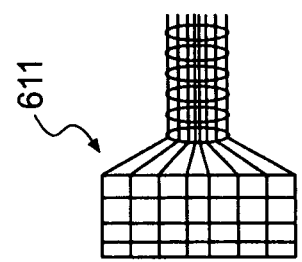
Figure 8J:
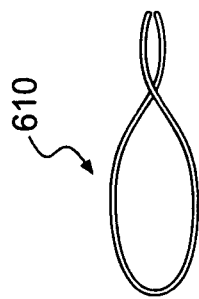
Figure 8O:
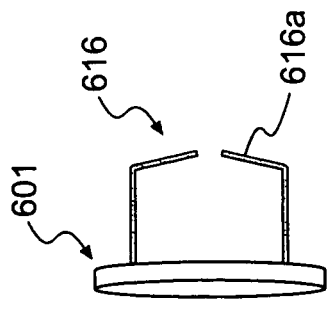
Figure 8R:
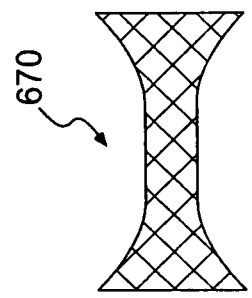
Figure 8N:
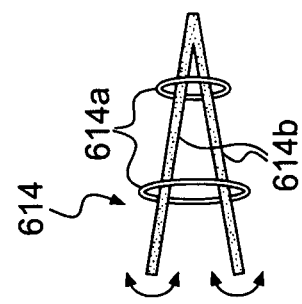
Figure 8Q:
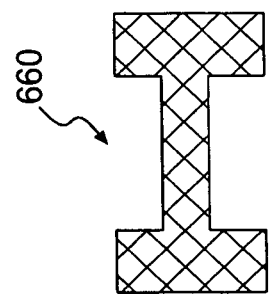

FIGS. 8A through 8O show various other exemplary fastening members according to various embodiments of the present invention. As shown in the figures, the fastening member can be formed of a flat plate 601 of virtually any geometric shape, a semispherical domed button 602, a flexible plate 603, a malecot 604, a ratchet 606, a non-orthogonal button 607, interconnectable multiple pieces 608, a foldable T-shaped bar 609, a twisted or tied coil, string, or other flexible elongate member 610, a stent-like configuration 611 wherein the connecting member has a crimped, braided configuration, a cotterpin 612, a rivot 613, a V-shaped clip 614, 615 with or without a flattened top (FIGS. 8N and 8P), a staple-like configuration (FIG. 8O), and stent-like connectors with dogbone or flared ends (FIGS. 8Q and 8R). Each fastening member connects to or comprises a connecting member 650.

These various fastening member embodiments will now be described in more detail. In an embodiment shown in FIG. 8D, the malecot 604 includes a plurality of legs or rods 604a that assume a cage-like shape when in its normal, expanded position. In another embodiment shown in FIG. 8F, the fastening member 606 includes at least one skirt-like or frustoconical-shaped ratchet 606 which permits movement only in one direction. In yet another embodiment shown in FIG. 8G, a non-orthogonal connection between the connecting member 650 and the fastening member 607, which may include any of the described fastening members, is provided. In still another embodiment shown in FIG. 8H, the fastening member 608 is formed of multiple pieces that are attached through any suitable means, such as piercing members or barbs. In still another embodiment shown in FIG. 8I, the fastening member 609 is pivotally coupled to the connecting member 650 to form a T-shaped configuration. Any conventional connecting devices and methods may be used to couple the fastening member 609 and the connecting member 650. In still another embodiment shown in FIG. 8J, the fastening member 610 is formed of a twisted or tied element. Preferably, the member 610 is made of a single piece and double-looped. In still another embodiment shown in FIG. 8K, the fastening member 611 is formed of a stent-like braided configuration. The middle portion of the configuration is crimped by a plurality of rings or is wrapped with a coil and constitutes the connecting member. In an expanded state, rings are removed or a coil is partially unwrapped at the distal end portion, or the distal end is not otherwise crimped like the connecting member portion, to form a fastening member 611 shown in the figure. FIGS. 8Q and 8R illustrate stent type fasteners 660, 670 respectively having a dogbone or flare shape at each end. These fasteners are deployed in a constricted manner and expanded or allowed to expand into a fastener comprised of a singular structure. The fasteners of FIGS. 8K, 8Q, and 8R may be constructed in any manner similar to fabricating stents as is known in the art, including but not limited to knitting, weaving, twisting, laser-cut tubes, welded wires and molding.

Figure 8M:
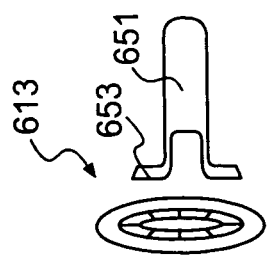
Figure 8P:
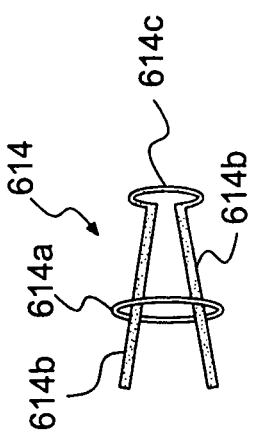

In still another embodiment shown in FIG. 8L, the fastening member 612 is formed of a bar or a plate, fixedly attached the connecting member by a cotterpin 612a or a stopper. In still another embodiment shown in FIG. 8M, the fastening member 613 is formed by attaching a rivot to the connecting member 651. In this case, the connecting member 651 includes an engagement member 653 protruding outwardly at its distal end, which engages the rivot to form the fastening member 613. In still another embodiment shown in FIG. 8N, the fastening member 614 is a clip having two or more legs 614b. The clip is expandable in a transverse direction, as indicated by arrows in the figure, thereby enhancing the tissue connection. Preferably, one or more bands or O-rings 614a are attached to limit the expansion to a desired extent and to abut the tissue layers. It should also be recognized that a plate or other flat surface 614c may be attached to, or otherwise be integral with, the expanded clip at its distal end, as shown in FIG. 8P.

In still another embodiment shown in FIG. 8O, the fastening member 616 forms a staple-like configuration. Similar to the embodiments shown in FIGS. 3-5, the wire 616a preferably forms a substantially straight wire in a contracted state and, in an expanded state, shown in the figure, the wire 616a expands outwardly or inwardly to form the staple-like configuration. Alternatively, an anvil can be placed behind tissue layers to bend the wires 616a and form the staple-like configuration. It should be recognized that more than two wires can be provided. Any other suitable designs providing the similar function may be utilized. In addition, the fastener may include any combination of fastening members and connecting posts.

In an embodiment, as shown in FIG. 8E, a tissue fastener 605 also may include a hollow bore 630 passing through the tissue fastener to inject a therapeutic chemical agent or an adhesion promoting substance. The tissue fastener is provided with an injection port 670 to permit introduction of the therapeutic substances or the adhesion promoting substance. The hollow bore 630 may be provided with a one-way valve (e.g., check valve) 672 to prevent a backflow. Fastener 605 may also comprise a weep hole 660 or other means along post 662 to allow delivery of the chemical agent or adhesion promoting means between the tissue layers.

Figure 10A:
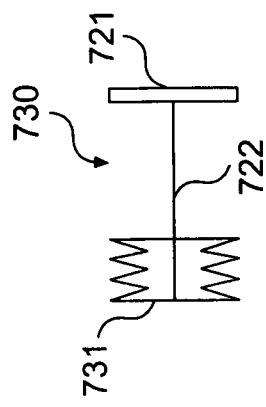
FIGS. 10A-10SS are perspective views of fasteners according to various embodiments of the present invention.
Figure 10A:
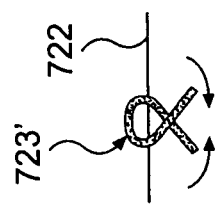

FIGS. 10A through 10OO show various other exemplary fastening members according to various embodiments of the present invention. These various embodiments, in addition to certain others described throughout this specification, adjust to varying tissue thickness so that sufficient tension, and in many embodiments substantially constant tension, is placed on the tissue to hold the tissue layers together. In many of the disclosed embodiments, such adjustment is performed by adjusting the length of the connecting member between the fastening members and/or by providing a means, in many cases associated with a fastener member, for providing a substantially constant tension on the tissue layers. Most of the embodiments shown in FIGS. 10A-10OO include a pair of opposed fastener members connected by a connecting member. It is to be understood that fastener members and connecting members of any embodiment may be used in combination with fastener members and connecting members of other embodiments, as desired.

FIG. 10A shows a "T"-shaped tissue fastener 720 having a first fastening member 721, a connecting member 722, and a second fastening member 723. Member 721 may comprise any suitable biocompatible elongate member, such as a portion of hypodermic tubing. Connecting member 722 may comprise suture material, wire, or any other like biocompatible material that fixedly connects to member 721, preferably in a fashion that permits member 721 to articulate with respect to connecting member 722 for ease of delivery and to the extent needed while implanted. Member 723 may comprise any bead or ball-shaped structure that permits connection to connecting member 722. Member 723 may include a slot therein permitting member 722 to slide through so that the length of member 722 between members 721,723 may be adjusted depending on the thickness of the connected tissue layers. For example, member 723 may be similar to a fishing weight having a slit therein to hold member 722. As an alternative and as shown in FIG. 10A', member 723 may be a torsion spring 723' having a pair of arms. When the arms are forced open in the direction of the arrows, connecting member 722 loosens from within spring 723' and spring 723' can slide relative to member 722 and be cinched against the tissue layers or an additional member 721. When the arms are released, spring 723' secures member 722 in position.

Figure 10B:
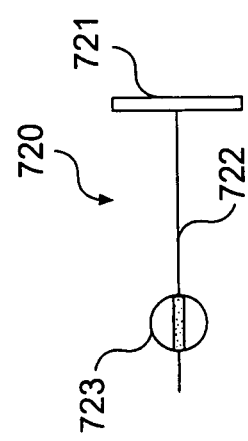
Figure 10B:
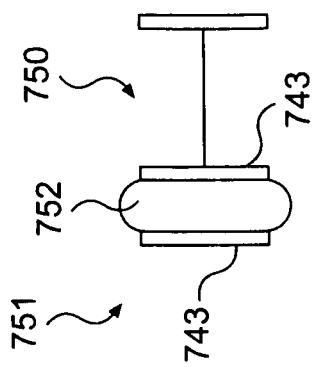

FIGS. 10B and 10B' show a tissue fastener 730 having first fastening member 721, connecting member 722, and a second fastening member 731 having a means for providing a substantially constant force on the tissue layers. In this case, the means includes a flexible bellows-like structure. The bellows of member 731 permit adjustment in the length of connecting member 722 between members 721 and 731. FIG. 10B shows the bellows of member 731 in an expanded, relaxed state. The bellows are contracted during delivery through the esophagus and to the tissue layers. Then, as shown in FIG. 10B', when fastener 730 is applied to tissue layers 735, the bellows will expand to place a sufficient force against the tissue layers to hold together those layers. In addition, through the use of the bellow-like structure, a substantially constant force is applied to the tissue layers, reducing tissue irritation or loosening of the tissue fastener.

Figure 10C:
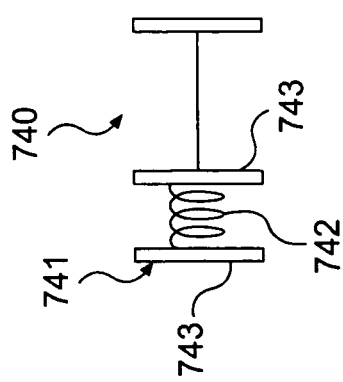
Figure 10D:
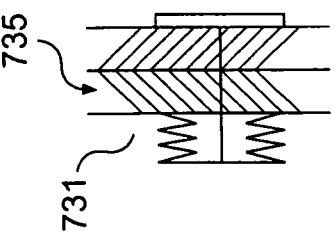
Figure 10X:
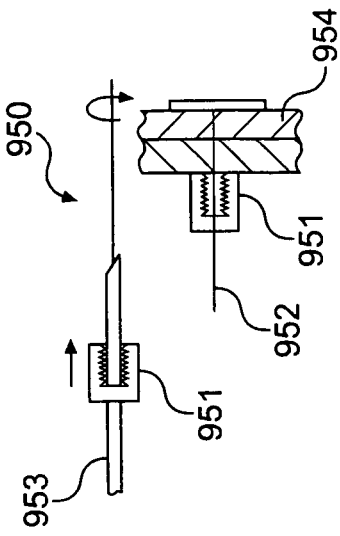
Figure 10W:
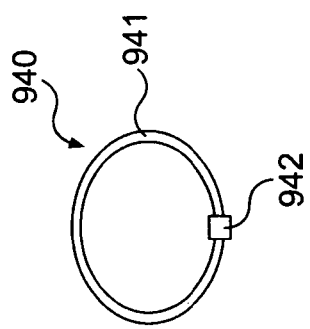
Figure 10V:
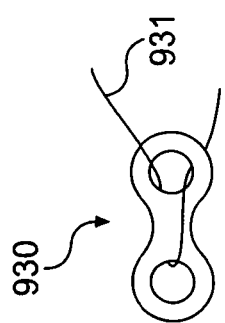
Figure 10A:
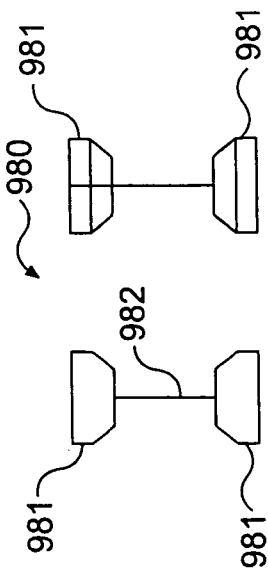
Figure 10Z:
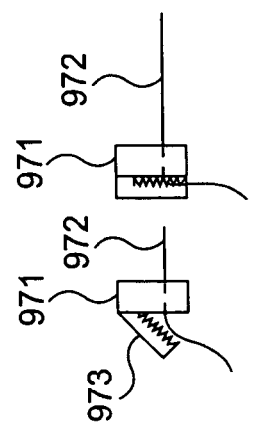
Figure 10Y:
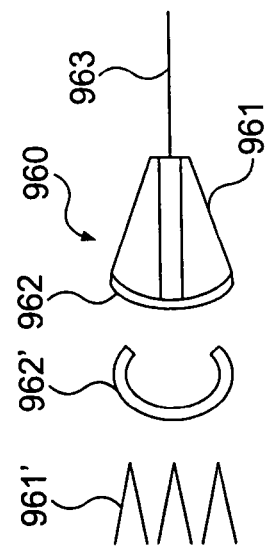
Figure 10H:
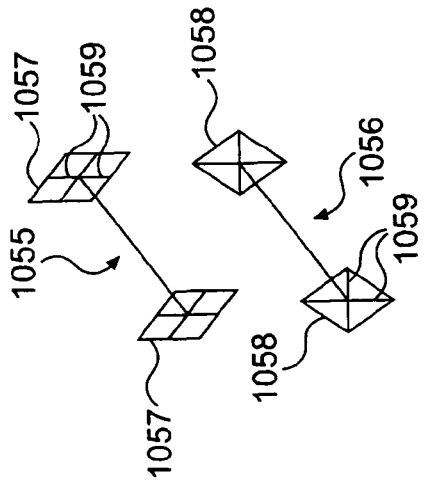
Figure 10I:
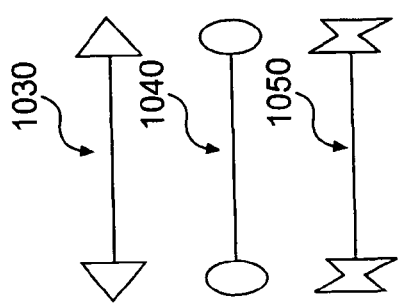

FIGS. 10C, 10D, and 10I show variations on means to maintain constant force on the tissue layers. In FIG. 10C, tissue fastener 740 includes a second fastener member 741 having a spring 742 between two plate-like structures 743, such as disks or buttons. In FIG. 10D, tissue fastener 743 includes a second fastener member 751 having a balloon 752 between the two structures 743. In FIG. 10I, tissue fastener 800 includes a second fastener member 801 having a spring 802. One end of spring 802 connects to structure 743 and the other end of spring 802 is free and places a substantially constant force against the tissue layers. Any suitable, biocompatible, compressible structure may take the place of spring 742, balloon 752, or spring 802.

FIG. 10E shows a "double-T" shaped tissue fastener 760 that is essentially of one-piece construction. Fastener 760 has two opposing fastener members 762, each taking the form of either member 721, member 743, or others described throughout this specification. Members 762 are connected by an elastic connecting member 761 that permits an adjustable length of member 761 between members 762. Member 761 may be made of a elastic, biocompatible material, similar to a rubber-band.

FIG. 10H shows a similar arrangement as FIG. 10E. Fastener 790 includes opposing fastener members 762 interconnected by a bungee cord-like member 792. Member 792 may be pulled tightly (elongated) between members 762 during delivery to the tissue layers and then released so that member 792 shortens and grows in diameter. The growth in diameter may permit an interference fit between member 792 and a hole, notch, slit, or other opening within one or both of the members 762, so that member 792 secures to members 762.

In addition to certain embodiments already described, other embodiments include structure associated with one or both fastener members to permit adjustment of the length of the connecting member between the fastener members. For example, FIG. 10F shows a fastener 770 having first and second fastener members 771, 772 and a connecting member 773. Member 773 includes a plurality of beads, balls, or similar enlarged structures 774 spaced along the length of member 773. As an alternative, the connecting member may include a plurality of notches spaced along the length of the member. The structures may be evenly or unevenly spaced as desired. The structures 774 may be used in combination with a frangible member 772 having a hole that permits structures 774 to travel through the hole to shorten the length of member 773 between members 771, 772. To place more a desired force on the tissue layers, additional structures 774 may be pulled through the hole in member 772. Member 772 may be constructed to include a notch therein to accommodate a structure 774. The through hole in member 772 may be constructed to permit passage of structures 774 in only one direction, i.e. away from member 771 to shorten the length of member 773 between members 771, 772. In addition, member 771 may have a similar construction as member 772 to permit passage of structures 774 therethrough. Excess connecting member 773 may be removed by any suitable method.

FIG. 10G shows a fastener 780 having a fastener member 781 with a ratchet-like mechanism to permit passage of connecting member 782 therethrough in one direction (shown by arrow). Thus, member 781 can move in the direction opposite the arrow to tighten fastener 780 on the tissue layers, with the ratchet-like mechanism preventing loosening of member 782 relative to member 781. Similarly, FIG. 10J shows a fastener 810 having a fastener member 811 with teeth 812 to capture connecting member 813 and prevent loosening. Teeth 812 may be angled in the direction of the applied force to more strongly grasp member 813.

Figure 10K:
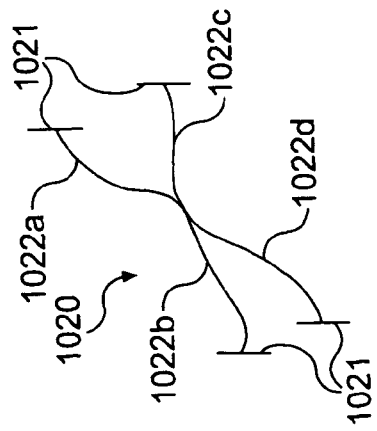
Figure 10J:
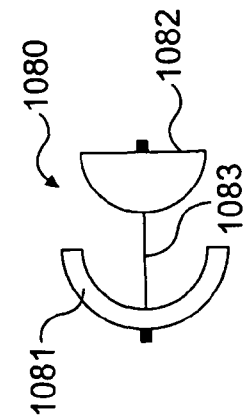

FIG. 10K shows a fastener 820 having a fastener member 821 with a biased locking mechanism 822. The lock 822 includes a ball bearing 823 or like structure contained within a through hole or passage of member 821, and a spring 824 biasing bearing 823 into the passage. Bearing 823 will lock connecting member 825 within the passage when member 825 is not being adjusted in length between the fastener members.

Figure 10L:
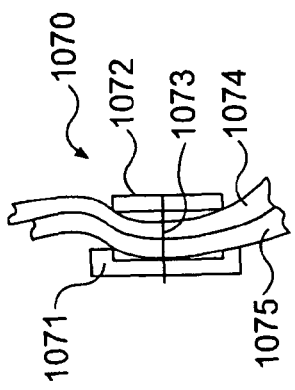
Figure 10M:
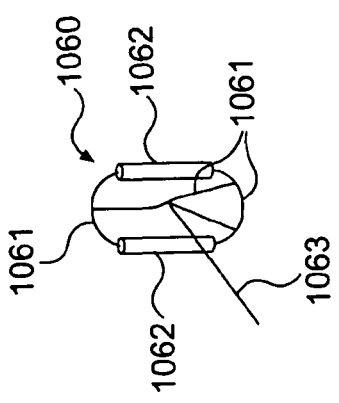

Alternative locking mechanisms are shown in FIGS. 10M and 10N. FIG. 10M shows a locking mechanism 840 that includes a pair of eccentric wheels 841 that rotate to lock connecting member 842 in position after member 842 is adjusted in length between fastener members, similar to eccentric wheel locking mechanisms used on sailboats. Mechanism 840 may be located within one or both fastener members of a fastener. FIG. 10N shows a similar arrangement, having a locking mechanism 850 with eccentric wedges used to lock connecting member 852 in position.

FIG. 10L shows a fastener 830 having a first fastening member 831, a connecting member 832, and a second connecting member 833. Member 833 has a two-piece construction that includes a disk 834 that snaps or otherwise fixedly attaches to a complementary dish-shaped head 835. After connecting member 832 is pulled through a passage in head 835 to adjust the length of member 832 between fastener member 831 and head 835, disk 834 is forced into and attached to head 835, securing member 832 in position.

FIGS. 10O and 10P show front views of exemplary fastener members 860 and 870 respectively. Member 860 includes a wedge-shaped opening 861 therein that accepts a connecting member. Member 871 has a wedge-shaped notch 871 in its side also for accommodating a connecting member. After being pulled taut within tissue and between fastener members, a connecting member may be pulled in the direction of the point of the wedge opening 861 or notch 871 to lock the connecting member in place.

FIG. 10Q shows a fastener 880 having a fastener member 881 having slots around its perimeter that accept connecting member 882. Member 881 may be twisted, as shown by the arrow, so that member 882 wraps around member 881 to adjust the length of member 881 between fastener members 881, 883. When the desired length is achieved, member 882 can lock in a notch or like structure on member 881.

FIGS. 10T and 10U show fasteners 910 and 920 respectively. Fastener 910 includes two dome-shaped fastening members 911 that fully invert in the deployed position (bottom of FIG. 10T) to exert additional force against the tissue layers. Similarly, fastener 920 includes two dome-shaped fastening members 921 that invert in their centers when in the deployed position (bottom of FIG. 10T) to exert additional force against the tissue layers.

FIG. 10V shows a fastener member 930 shaped in a figure eight and having two openings. A connecting member 931 may be adjusted in length between fastening members by winding member 931 around and through the openings, similar to a rappel loop. A small notch in member 930 may hold member 931 once member 930 has been drawn to the desired tension.

FIG. 10W shows a fastener 940 that includes a loop 941 and a connection member 942. Loop 941 may comprise a cable, wire, or other suitable biocompatible material. Loop 941 extends through the tissue layers twice and joins at its ends at connection member 942, which may be located on either side of the tissue layers, through any suitable means. Loop 941 may be tightened and excess loop portions may be excised by cutting or any other suitable method. This embodiment results in a relatively small footprint at the tissue layers.

FIG. 10X shows a fastener member 951 that is a spring clip. Once connecting member 952 is adjusted to the desired tension, spring clip 951 may be inserted over a needle 953 through which connecting member 952 extends (see top portion of FIG. 10X). Spring clip 951 is extended past the distal end of needle 953 to grasp connecting member 952 adjacent tissue layers 954 (see bottom portion of FIG. 10X).

The right-hand side of FIG. 10Y shows a deployed fastener 960 that includes a collet 961 and a C-spring 962. The left-hand side of FIG. 10Y shows collett 961 and C-spring 962 in undeployed positions, i.e. in an open mode. Much like open drill bit chuck, collett 961 can fit over any size connecting member 963. Once collet 961 is in position over connecting member 963 and C-spring 962, or an O-ring or other like structure, is slipped over collet 961, collet 961 closes on member 963. This embodiment permits fastener adjustments.

FIG. 10Z shows a fastener member 971 in both an open position (left-hand side) and a closed position (right-hand side). Member 971 includes a cap 973 with teeth to grip a connector member 972. Cap 973 is held to the remainder of member 971 by a hinge, such as a living hinge. Pulling member 972 opens cap 973 enough to let the connector member 972 adjust. Cap 973 snaps back down to secure member 972. The exit of connecting member 972 from cap 973 could be at a slot or notch at an edge of cap 973.

As shown in the variations of FIGS. 10DD and 10EE (showing end views of alternative fasteners 971 with caps 973' and 973" respectively), the exit of connecting member 972 from cap 973', 973" could be at a through hole 974 off-center from the fastener hole 975 (FIG. 10DD) or a slot 976 in cap 973 offset from fastener hole 975 (FIG. 10EE). In these alternative embodiments, pulling member 972 to adjust its length will open the cap 973', 973" slightly.

FIG. 10AA shows a fastener 980 in the undeployed (left-hand side) and deployed (right-hand side) states. Fastener 980 includes fastener members 981 connected by a connecting member 982. Members 981 have an inward wedge shape that will displace some force to friction along an axis of the connecting member 982. The wedge increases surface area contact of the fastener member 981 with the tissue layers and therefore friction between the layers and the member 981. The wedge portion may include a fabric surface to increase friction. The area of the fabric may be made larger than the surface area of the wedge so that the fabric may bunch up to further increase surface area and friction. A fabric surface or covering may be placed over any suitable fastener member described herein.

FIG. 10BB shows a fastener 990 having a fastener member 991 and a connecting member 992 attached at its ends to fastening members 993. Member 991 may be a pledget or any other suitable member described herein or known in the art. Members 993 may be similar to member 921 described above in connection with FIG. 10A. In FIG. 10BB, member 992 extends through the tissue layers and member 991 in two places. After deployment of fastener 990, the portion of member 992 extending through member 991 may be twisted (as shown by the arrow) to place desired tension against the tissue layers. Connecting member 992 may be similar to member 722 of FIG. 10A and may be a polymer suture so that ultrasonic or other energy may be used to fuse the twisted portion together by melting.

As a variation of the embodiment of FIG. 10BB, FIG. 10CC shows a fastener 990' having a suture-like member 992 that extends through member 991 and is formed into a z-like pattern 994 on a surface of member 991 away from the tissue. Member 992 tightens between members 991 and 993 as member 992 is pulled in the direction of the arrows. As a further variation of the embodiment shown in FIG. 10BB, FIG. 10S shows a fastener 900 similar to fastener 990 except that fastener 900 has a one-piece second fastener member 902.

FIGS. 10FF, 10GG, and 10HH show variations of "r-shaped fastener embodiments. Fastener 1000 includes fastener members 1002 each in the shape of an "H" connected by connecting member 1001. Fastener 1010 includes "T" shaped fastener members 1011 connected by a connecting member that splits into three portions 1012a, 1012b, and 1012c. Fastener 1020 is much like fastener 1010 and includes "T" shaped fastener members 1021 connected by a connecting member that splits into four portions 1022a, 1022b, 1022c, and 1022d. As with all of the embodiments described herein, any combination of fasteners and connecting members from FIGS. 10FF-10HH may be used to form a suitable fastener.

FIG. 10II shows various embodiments of fasteners 1030, 1040, 1050 that include wire frames as fastener members. The wire frames may be configured in any suitable shape, including triangular, round, and irregular, as shown. It is preferable that the wire frame be collapsible into a flattened shape for ease of delivery and then expand upon deployment.

FIG. 10JJ shows embodiments of fasteners 1055, 1056 having fastener members 1057, 1058 in kite-like configurations. The fastener members 1057, 1058 may include a combination of wire material on the external perimeter portions and suture material as the spokes 1059 extending form the connecting members to the wire perimeter. The fastener members may be configured in any suitable shape, including square, diamond, etc., and, as in the FIG. 10II embodiments, collapse into a flattened shape for delivery and expand upon deployment.

FIG. 10KK shows a fastener 1060 made of a combination of suture material 1061 connecting a pair of hypotubes 1062. the suture material connects to a connecting member 1063 at an approximate midpoint of the fastener 1060. The suture material in the embodiments of FIGS. 10JJ and 10KK, and any other embodiments disclosed herein, may be elastic, fuzzy (like dental floss), and/or swell upon deployment.

FIGS. 10LL-10OO show various embodiments of fasteners designed to have an increased footprint on the tissue layers. When each of these embodiments is used in a fundoplication procedure, a button is placed on the esophageal side of the tissue layers and a mating cup is placed on the stomach side. These arrangements spread force on the tissue layers beyond the button and prevent pull-through in the esophagus. For example, Figure LL shows a button-shaped fastener member 1072 adjacent esophageal tissue 1074 and a mating cup fastener member 1071 adjacent stomach tissue 1075. A connecting member 1073 extends between button 1072 and cup 1071. FIGS. 10MM-10OO show other shaped buttons and mating cups. FIG. 10MM shows fastener 1080 with a convex cup 1082 connected by a connecting member 1083 to a concave mating cup 1081. FIG. 10NN shows fastener 1090 with a wedge-shaped cup 1092 connected by a connecting member 1093 to a corresponding mating cup 1081. FIG. 10OO shows fastener 1100 with a convex cup 1102 connected by a connecting member 1103 to a concave mating cup 1101 surrounded by a flattened area 1104 that further increases the footprint on the tissue layers. Convex, wedge, and other like-shaped buttons increase tissue contact area relative to a flat button arrangement. Other shaped buttons and mating cups may be used.

FIG. 10PP shows a fastener 1110 in a delivered state (top) and a deployed state (bottom). Fastener 1100 is a tube or rod that includes a plurality of slits at ends 1111. Upon deployment at the desired site, the slits at the ends permit the ends to attain a fastener member arrangement having a plurality of arms 1112. Such deployment may be attained through a shape memory material, a deployment mechanism that separates the slits to form arms 1112, or any other suitable method. FIG. 10QQ shows a variation of the fastener embodiment shown in FIG. 10PP. Fastener 1120 includes a pointed, slotted end 1121 that, when deployed, shapes into arms 1122. The pointed end may permit puncturing through the tissue layers. The pointed tip may remain, may be removed through any mechanical, thermal or other suitable method, or may be made of a absorbable material.

FIG. 10RR shows a fastener 1130 that includes a connecting member 1132 with expandable fastener members 1131 at each end. The top portion of FIG. 10RR shows the delivered state in which members 1131 remain in a collapsed configuration, and the bottom view shows members 1131 in a deployed configuration. Members 1131 may be balloons and may be expanded by fluid actuation or any other suitable method. Like fastener 1120, fastener 1130 may be modified to include a pointed tip.

FIG. 10SS shows fasteners 1140 and 1150 having fastener members 1141, 1151 respectively that include non-straight connector pathways. Such pathways create an interference between the connecting member 1142, 1152 and the member 1141, 1151 to aid in securing them together. In the embodiments shown, member 1141 includes a wavy, or serpentine, pathway for member 1142, and member 1151 includes a pathway with a bend. Other non-straight pathways may be used.

FIG. 10R shows a fastener 890 having a plurality of connecting members 891 across the tissue layers to spread the force applied to the tissue surfaces. The connecting members 891 may be unconnected at their ends, or may be connected at their ends to be a single member wrapped around the fastener members 892, 893.

In further embodiments, friction between the connector member and the fastener members may be increased by a rough surface on the connector member (by for example braiding, knots, fibers), an elastic connecting member, a coated connecting member, or a fabric covered connecting-member. In addition, the through hole of the fastener member(s) may include gripping teeth arranged at an angle to prevent reverse movement of the connecting member. Embodiments as appropriate throughout this specification also may include a quick-setting, water tolerant adhesive or glue, such as cyanoacrylate, may be used to pack the passage or hole within a fastening member.

Figure 9B:
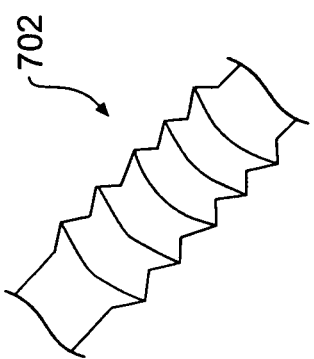
FIGS. 9A-9J are perspective views of various connector post designs according to still other embodiments of the present invention.
Figure 9E:
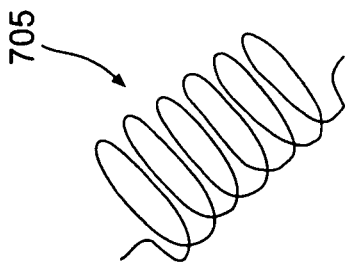
Figure 9A:
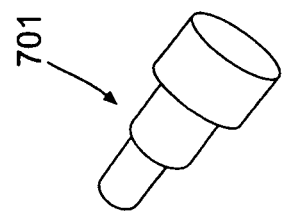
Figure 9D:
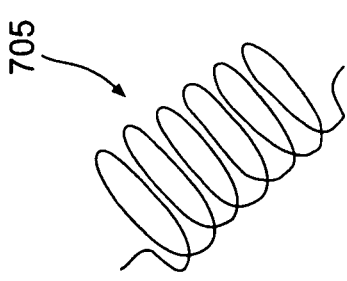
Figure 9C:
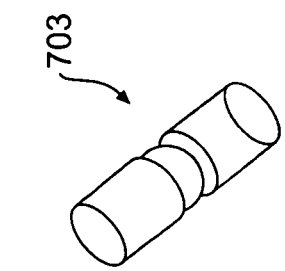
Figure 9G:
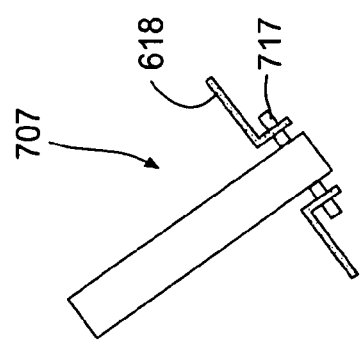
Figure 9F:
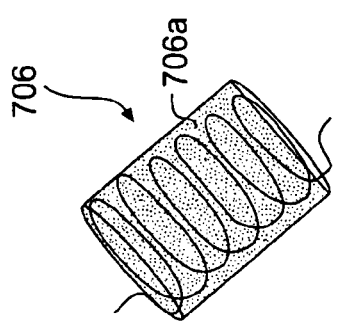
Figure 9J:
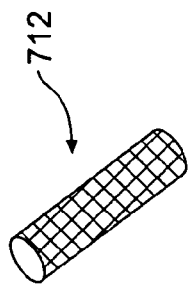
Figure 9I:
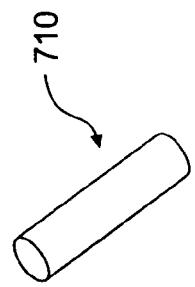
Figure 9H:
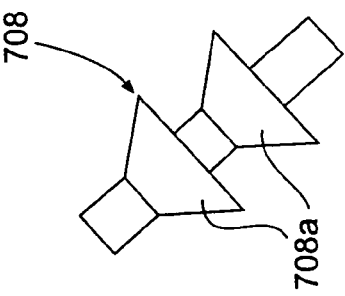

FIGS. 9A through 9J show various other exemplary connecting members according to other embodiments of the present invention. As shown in the figures, a connecting member can be formed of a telescopic bar 701, a collapsible bellows 702, a cylindrical bar with a ball-socket arrangement 703, a stent-like braided configuration 704, a spiral-shaped spring 705, a webbed spiral spring 706, a crimped structure 707, ratchet 708, elastic member 710, or webbed member 712. In particular, at least the connecting members 701, 702, 705, 706, 710, and 712 shown in FIGS. 9A, 9B, 9E, 9F, 9I, and 9J are configured to be expandable/contractible so as to provide compressive forces to enhance fastening. In an embodiment shown in FIG. 9E, the connecting member 705 is formed of a spiral-shaped spring. As shown in FIG. 9F, the spiral-shaped spring may be covered with a conforming material 706a, such as, for example, polyurethane, silicone, polytetrafluoroethylene, webbed material or other suitable material. In another embodiment shown in FIG. 9G, the connecting member 707 is configured to be coupled to a fastening member 618. Preferably, a pledget 717 or a ring is utilized to couple between the connecting member 707 and the fastening member 618 to allow moveability of the fastening member 618 along the connecting member 707. In yet another embodiment shown in FIG. 9H, the connecting member 708 includes at least one skirt-like or frustoconical-shaped ratchet 708a which permits movement only in one direction. FIG. 9I illustrates a post embodiment wherein the post comprises an elastic material. The embodiment of FIG. 9J illustrates a post 712 comprising a webbed material, for example, a knit or woven material. Any other suitable designs providing the similar function may be utilized.

A connecting member 701-712 is preferably strong enough to maintain its integrity and utility even under stressful events, such as running, swimming, sneezing, coughing, vomiting, or the like. These connecting members 701-712 can provide compressive forces to enhance the fastening of the tissues. In addition, these connecting members 701-712 provide enhanced flexibility for traversing through a tortuous path within a body.

Many of the disclosed tissue fasteners, especially those that expand from a contracted, delivered state to an expanded, deployed state, may be made of a shape memory material, such as, for example, nickel titanium alloy (e.g., Nitinol) or a polymer. By utilizing a shape memory material, the fastening member is able to transform from its delivered state to its deployed, functional state automatically upon deployment. Alternatively, the reconfiguration can be obtained by utilizing a material that is reactive to a predetermined condition, e.g., temperature, pH, electrical current, and/or a number of other internal and external stimuli or by its material properties such as elasticity. The expandability of the distal and proximal fastening members can also be obtained by utilizing any suitable mechanical means, such as, for example, a manually actuated expander.

The disclosed tissue fasteners are preferably composed of a biocompatible and biocompliant material, i.e. similar to the compliance of the tissue being connected. The fasteners also may be coated with thrombogenic agents and therapeutics to prevent tissue inflammation. Examples of materials for a tissue fastener, including its coating or covering, include silicone-based polymers, nylon-based polymers, hydrid Teflon-textile based polymers, polypropylene, polyethlylene, or growth factors. Polymer coating materials further include polycarboxylic acids, cellulosic polymers (e.g., cellulose acetate and cellulose nitrate), gelatin, polyvinylpyrrolidone, cross-linked polyvinylpyrrolidone, polyanhydrides (e.g., maleic anhydride polymers), polyamides, polyvinyl alcohols, copolymers of vinyl monomers (e.g., EVA), polyvinyl ethers, polyvinyl aromatics, polyethylene oxides, glycosaminoglycans, polysaccharides, polyesters (polyethylene terephthalate), polyacrylamides, polyethers, polyether sulfone, polycarbonate, polyalkylenes, halogenated polyalkylenes (e.g., polytetrafluoroethylene), polyurethanes, polyorthoesters, proteins, glycoproteins, recombinant proteins, polypeptides, silicones, siloxane polymers, polylactic acid, polyglycolic acid, polycaprolactone, polyhydroxybutyrate valerate and blends and copolymers thereof, coatings from polymer dispersions such as polyurethane dispersions (e.g., BAYHDROL®), fibrin, collagen and its derivatives, polysaccharides (e.g., celluloses, starches, dextrans, alginates and derivatives), hyaluronic acid, and squalene emulsions. Other preferred materials include polyacrylic acid (e.g., HYDROPLUS®), described in U.S. Pat. No. 5,091,205, the disclosure of which is hereby incorporated by reference, and a copolymer of polylactic acid and polycaprolactone. In a preferred embodiment, the fastener comprises a bioabsorbable material. A preferred coating would be one which would minimize tissue inflammation around the fastener.

The disclosed tissue fastener can be made of biodegradable, bioresorbable, and/or bioabsorbable material. The clamping force created by the fastener will induce adhesion formation between the tissue layers. This can occur in a controlled fashion by carefully selecting a material with a predetermined degradation rate. The bioabsorbable material may be formed of cross-linked polymer networks that can be manufactured to be responsive to body temperature, light, pH, and/or a number of other external/internal stimuli.

Deployment of a tissue fastener is discussed below with reference to an exemplary endoluminal deployment system, shown in FIGS. 11A-C. For illustration purpose, the tissue fastener 1 shown in FIG. 2 is used to illustrate various deployment stages of a tissue fastener, according to an embodiment of the present invention. The deployment system, however, may be used with various other embodiments of tissue fasteners described above. The deployment system 50 includes a flexible overtube 52 configured to accommodate a tissue fastener 1 in a delivered state, and a coupling mechanism 53 for grasping and moving the tissue fastener 1 along the lumen of the overtube 52. The deployment system 50 may also be configured to accommodate multiple tissue fasteners that are stacked axially. The coupling mechanism may be a mechanical grasper 53 that is remotely operable by suitable actuation means at the proximal end (not shown) of the overtube 52. The system 50 also includes a pusher 54 for guiding the tissue fastener along the overtube 52. The pusher 54 may include a hollow lumen through which a cable for operating the grasper 53 passes. The overtube 52 includes a lumen 56 preferably having a diameter capable of accommodating the tissue fastener 1. In at least one embodiment, the overtube 52 may be incorporated into a conventionally known endoluminal fundoplication device, described in U.S. Pat. No. 6,086,600, the disclosure of which is hereby incorporated by reference. A device as taught in that patent may be used to fold the esophageal and fundus walls together, with overtube 52 then used to apply one or more fasteners. The overtube 52 is preferably made of polymer, polymer reinforced with metal, or metal hypotube. The overtube is preferably low in profile and flexible enough to traverse the cricopharyngeal area transorally.

FIGS. 18A and 18B show an exemplary embodiment of deployment system 50, wherein a grasper 53 is fixedly connected to a distal end of a pusher 54. Grasper 53 includes a pair of arms 53' each terminating in bent hooks 53". Arms 53' are elastic and biased in the open position shown in FIG. 18B. During delivery of a tissue fastener, arms 53' are contracted within overtube 52, ands hooks 53" mate with a head 11' of fastener member 11 to hold the fastener to be deployed. When the fastener is deployed and pusher 54 is moved distally so that grasper arms 53' move past the end of overtube 52, arms 53' bias to the open position and release member 11. Other suitable coupling methods and devices known in the art for mechanically or otherwise coupling a tissue fastener to a delivery mechanism may be used, such as for example, graspers, pull wires, hooks, elastic couplings, springs, cups, and hypotubes.

In another method of detaching a tissue fastener, such as a fastener made of a single wire or any other suitable fastener described in this disclosure, the fastener may be attached to an external mechanism, such as a wire, that runs outside the body. The external wire then may carry the electrical current to electrically detach the fastener when installation of the tissue fastener is complete. Technology known as a Gugliemi Detachable Coil (GDC) or GDC coil detachment, such as that described in U.S. Pat. No. 5,423,829, incorporated by reference herein, may be used in connection with this embodiment.

Referring back to the embodiment shown in FIG. 11B, the tissue fastener 1 is contained within the flexible overtube 52 and endoluminally delivered to a desired site in a body to protect the body lumen from possible damage caused by the sharp edge 15 of the tissue fastener 1. As shown in FIG. 11B, once the distal end opening 55 of the overtube 52 is placed at the desired site, the tissue fastener 1 is advanced toward the tissue surface, such that the sharp edge 15 of the tissue fastener 1 makes contact with the tissues to be perforated. It should be understood that the tissue fastener may be configured to perforate through the tissue layers, or may be configured to pass through an opening already made by other perforating instruments or the overtube 52. For example, the overtube may include a sheath covering it to puncture through tissue. Once the tissue fastener 1 passes through tissue layers, the distal fastener member 13 is further advanced out of the overtube 52, and the anchor legs 23 are expanded outwardly to form an umbrella-shaped fastening member 13, as shown in FIG. 11C, to hold the tissue layers together.

Figure 12A:
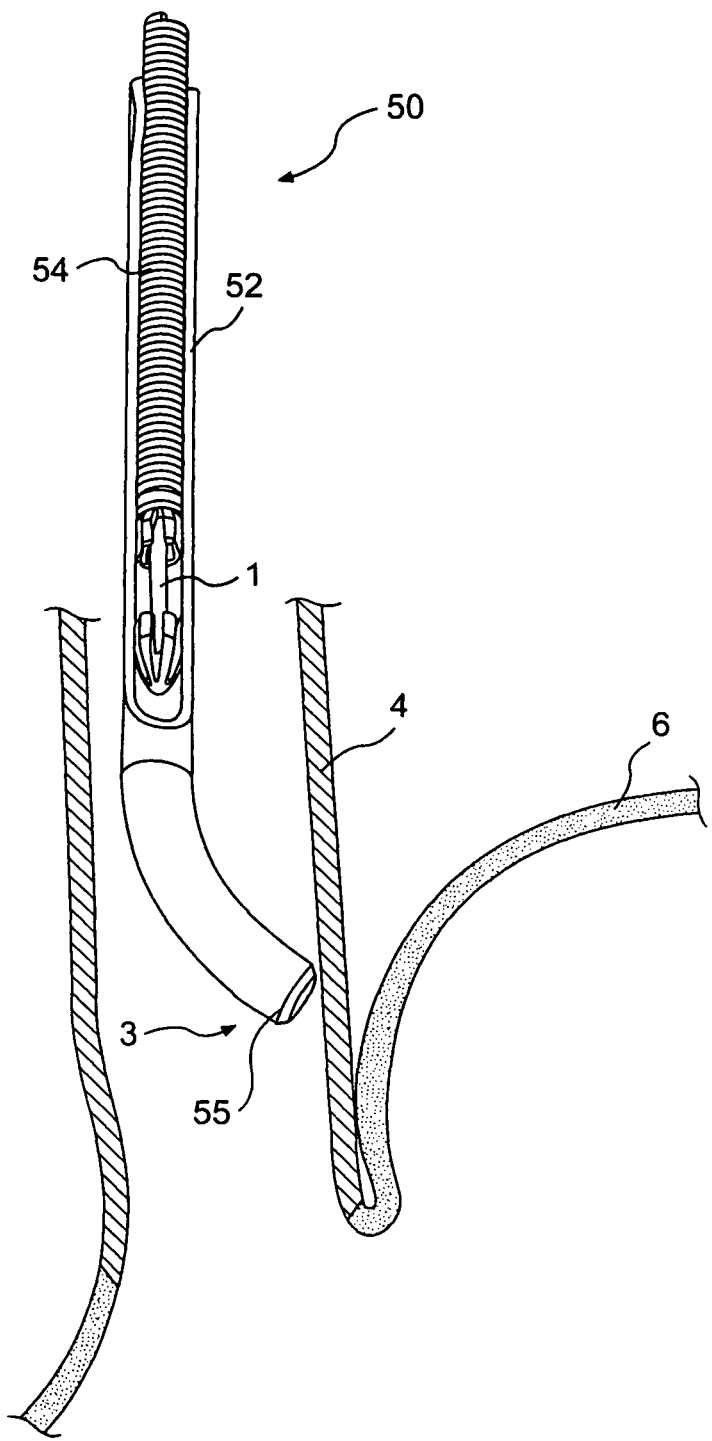
FIG. 12A is a schematic illustration of the tissue fastener deployment for a tissue connection procedure, showing the deployment system of FIGS. 11A-C containing the tissue fastener of FIG. 2 and being inserted into the lower esophagus, according to an embodiment of the present invention.

FIGS. 12A through 16 show implantation of a tissue fastener 1 in a fundoplication procedure, using the endoluminal deployment system shown in FIGS. 11A-11C. The deployment includes performing the delivery and placement of the tissue fastener 1 in essentially one step. As shown in FIG. 12A, the deployment system 50 containing the tissue fastener 1 is transorally inserted into the lower esophagus 3 and positioned adjacent to a desired location near the distal end of the esophagus 3 for the fundoplication procedure.

Preferably, prior to the insertion of the endoluminal deployment system into the esophagus 3, the fundus wall 6 is lifted and folded toward the esophageal wall 4 as shown in FIG. 12A. Any suitable mechanism for lifting the fundus wall 6 toward the esophageal wall 4 may be used for this purpose. An example of such a suitable device is shown and described in U.S. Pat. No. 6,086,600, the entire disclosure of which is incorporated by reference herein. It should also be understood that the lifting device may be formed in combination with the endoluminal deployment system 50.

Figure 12B:
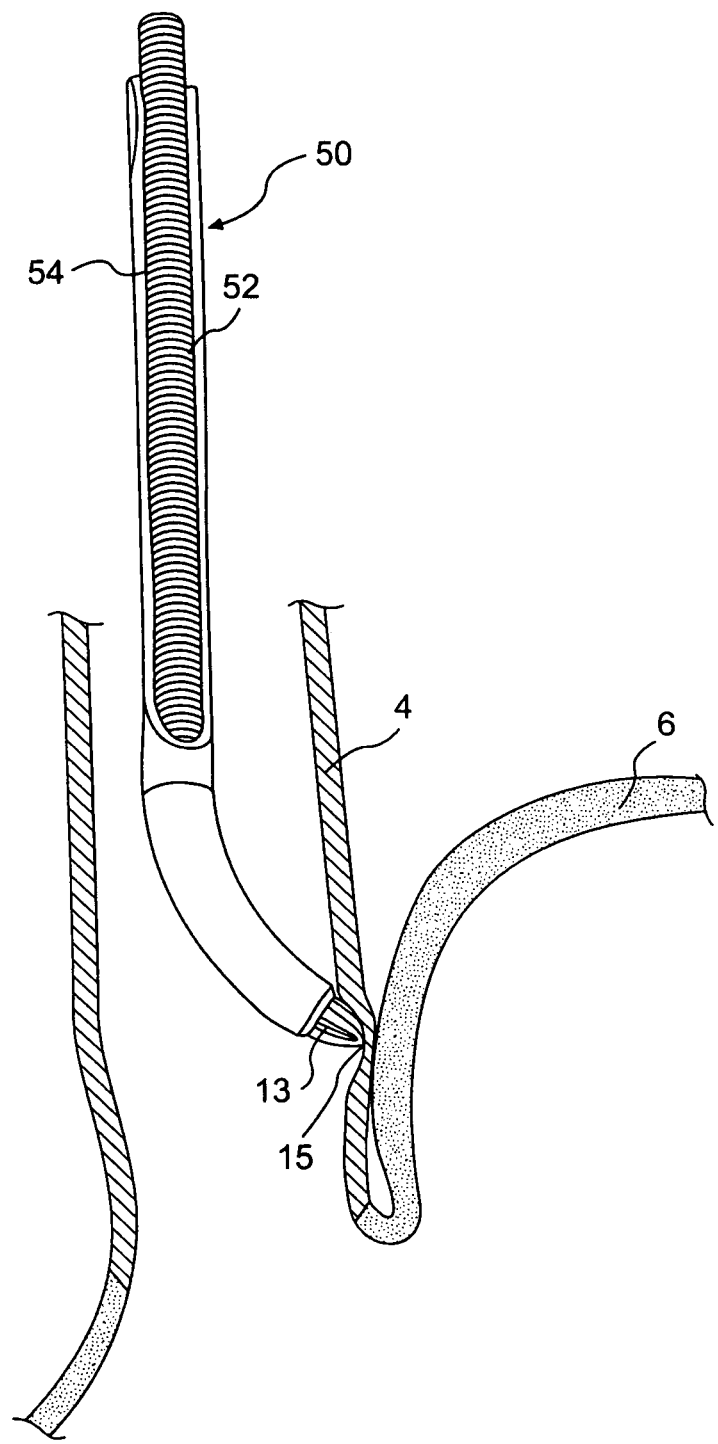
FIG. 12B is a schematic illustration of the tissue fastener deployment, showing the deployment system penetrating the esophageal wall, according to an embodiment of the present invention.
Figure 13:
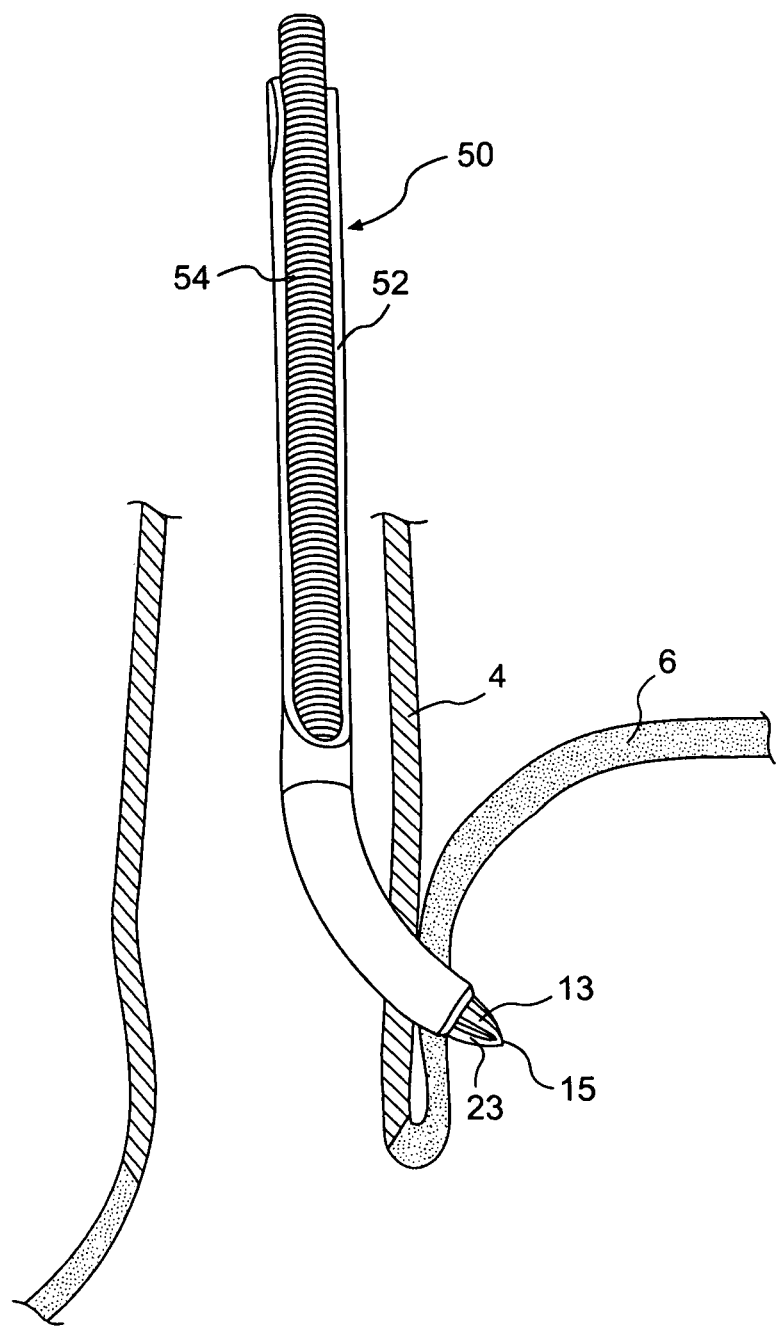
FIG. 13 is a schematic illustration of the tissue fastener deployment, showing the deployment system penetrating the esophageal wall and the fundus wall, according to an embodiment of the present invention.

After the distal end opening 55 of the overtube 52 positioned proximate a desired perforation site of the esophageal wall 4, the tissue fastener 1 is advanced toward the esophageal wall surface, such that the sharp edge 15 of the tissue fastener makes contact with the surface, as illustrated in FIG. 12B Tissue fastener 1 preferably extends out of the overtube 52 only enough so that the edge 15 extends from the opening 55, yet a portion of legs 23 remain in the overtube 52 so that the distal fastening member 13 remains in a contracted state. As discussed above, the tissue fastener 1 may be configured to cut through the esophageal wall 4 and the fundus wall 6, or may be configured to penetrate through an opening already made by other instrument or the overtube 52. As shown in FIG. 13, the overtube 52 with the sharp edge 15 of the tissue fastener 1 protruded out of the overtube 52 is advanced through the esophageal wall 4 and the fundus wall 6.

Figure 14:
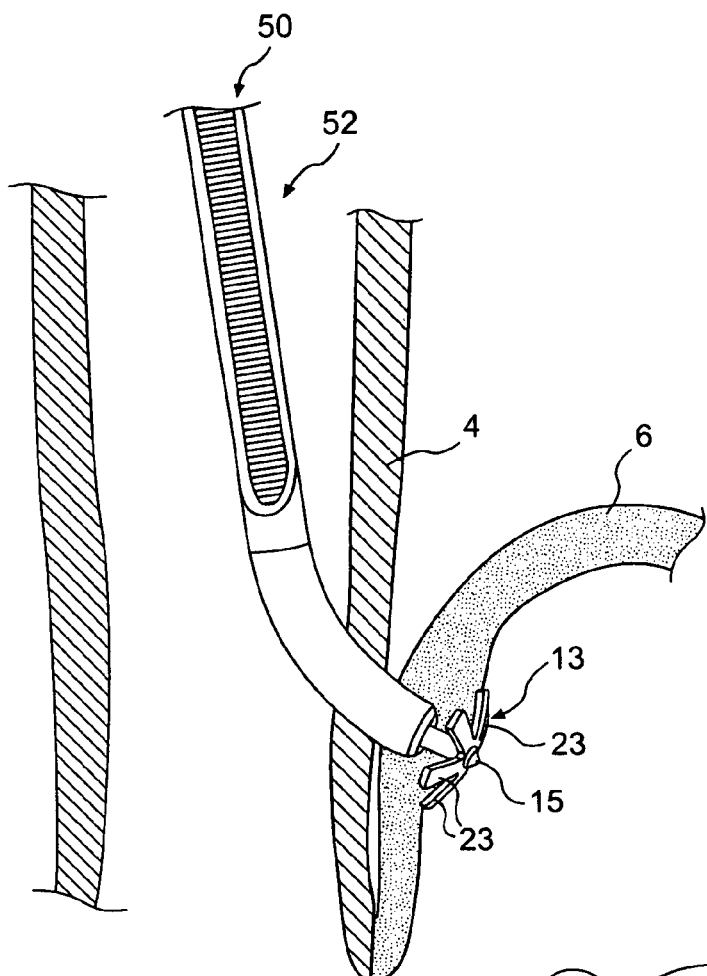
FIG. 14 is a schematic illustration of the tissue fastener deployment, showing the expanded distal fastener member of the tissue fastener holding the fundus wall, according to an embodiment of the present invention.
Figure 15:
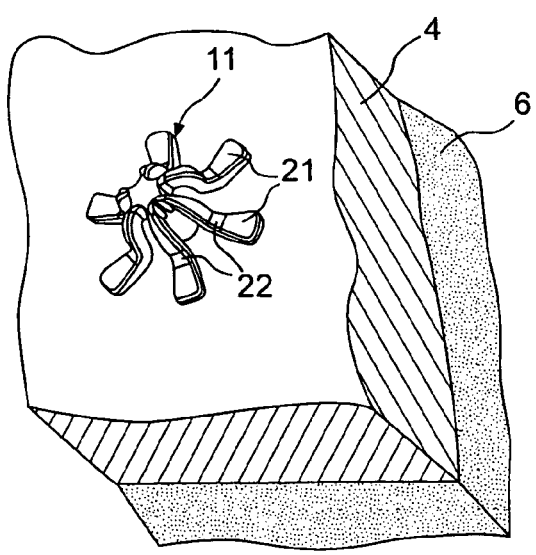
FIG. 15 is a perspective view of a proximal fastening member of the tissue fastener of FIG. 2, viewing from inside the esophagus, after the deployment is complete, according to an embodiment of the present invention.

Once the tissue fastener 1 passes through the layers of esophageal and fundus walls 4, 6, the distal fastening member 13 of the tissue fastener 1 is further advanced out of the overtube 52 causing the anchor legs 23 of the distal fastening member 13 to expand outwardly to form an umbrella-shaped fastening member 13, as shown in FIG. 14. After the distal fastening member 13 is securely placed against the inside fundus wall 6, the overtube 52 is withdrawn and releases the tissue fastener 1 to completely expose the proximal fastening member 11 of the tissue fastener 1. The anchor legs 21 of the proximal fastening member 11 expand outwardly to form the fastening member 11. FIG. 15 is a perspective view of the proximal fastening member 11 of the tissue fastener 1, viewing from inside the esophagus, after the deployment is complete. The distal fastening member 13, i.e., the gastric side, should be robust and resistant to low stomach pH, and the proximal fastening member 11, i.e., esophageal side, should be low in profile to prevent possible lumen occlusion.

Figure 16:
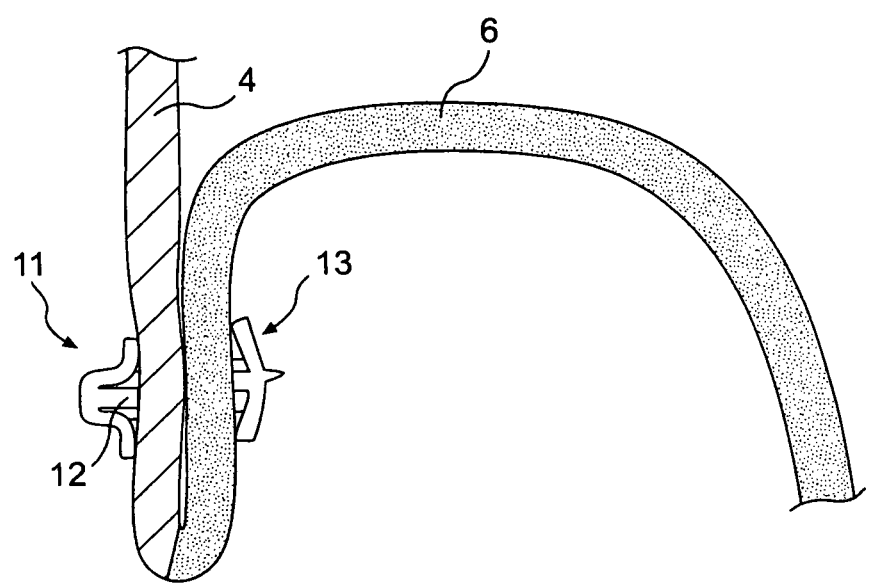
FIG. 16 is a cross-sectional view of the esophageal wall and the fundus wall, with a tissue fastener in place, after the tissue connection procedure.

FIG. 16 is a cross-section view of the esophageal wall 4 and the fundus wall 6, with a tissue fastener in place, after the fundoplication procedure is complete. The expanded distal and proximal fastener members 13, 11 of the tissue fastener 1 hold and maintain the esophageal and fundus walls 4, 6 together in place to create the fundoplication. The tissue fastener 1 should be strong enough to hold the esophagus and fundus together with a force of approximately 6 lbs without damage to the esophageal wall 4 or fundus wall 6. Furthermore, the tissue fastener 1 should be sufficiently strong enough to maintain its integrity and utility even under stressful events, such as running, swimming, sneezing, coughing, vomiting, or the like. Depending on the type of tissue fasteners used and the desired fastening strength, more than one tissue fastener may be installed. In that instance, a deployment system capable of loading multiple tissue fasteners can be used.

The invention is not limited to the exemplary embodiment used to illustrate the deployment of the tissue fastener 1. Other various tissue fasteners encompassed in this disclosure can be used with the deployment systems and methods described above. Moreover, the disclosed tissue fasteners of the present invention can be used with any other deployment mechanisms conventionally known in the art. In particular, for the tissue fasteners 301, 401 that do not encompass sharp cutting edges, an opening through the esophageal wall 4 and the fundus wall 6 can be made by other piercing instruments, or the endoluminal deployment system 70 having a cutting edge 40 on its distal tip, as shown in FIGS. 17A and 17B.

FIGS. 17A and 17B illustrate endoluminal deployment systems 70 used for the disclosed tissue fasteners, according to still other embodiments of the present invention. Similar to the deployment system 50 shown in FIGS. 10A-C, the deployment system 70 shown in FIGS. 17A and 17B includes a flexible overtube 71 having either a straight or curved distal portion and configured to accommodate a tissue fastener 70 in a contracted state. Fastener 70 is represented with fastening head 74 and connector 72, but this illustration is not intended to limit the possible embodiments. In this embodiment, overtube 71 is represented as a needle. Overtube 71 may be of any size necessary to deploy fastener 71 while working within the confines of anatomical space and instrument space needed to fold and retain the fundus against the esophageal wall. The overtube 71 includes an opening 45 at its distal tip, through which a tissue fastener passes. The opening 45 is defined by a slanted edge to form a sharp cutting edge 40. During deployment, the sharp cutting edge 40 forms an opening through the tissue layers prior to the deployment of a tissue fastener. The fastener 70 is deployed by releasing a fastening head on one side of the tissue layers undergoing attachment and withdrawing overtube 71 from the tissues to release a second fastening head on the opposite tissue layer side.

Other devices and methods for delivery and deployment of tissue fastener disclosed herein may be used. Suitable, exemplary methods and devices are disclosed in U.S. application Ser. No. 10/230,682 of Robert Devries et al., filed on Aug. 29, 2002, now U.S. Pat. No. 7,083,630, and entitled "Devices and Methods for Fastening Tissue Layers." The complete disclosure of that application is incorporated by reference herein.

In addition, although the present invention is depicted in this disclosure as being used in the treatment of GERD, e.g., a fundoplication procedure, it is to be understood that the tissue fastener and related deployment methods and systems of the present invention can be used to treat any of a number of different disease conditions, and can be used for fastening any desired body tissues.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A delivery system configured for deployment of an expandable tissue fastener, comprising:
   a tissue fastener having a proximal member configured to expand from a delivered state to a deployed state, a distal member configured to expand from a delivered state to a deployed state, and an elongate connecting member connecting the proximal member to the distal member;
   a flexible tube having a lumen configured to accommodate the tissue fastener in a contracted state;
   a pusher for guiding the tissue fastener along the lumen of the tube; and
   a grasper coupled to a distal end of the pusher and configured to grasp the tissue fastener, the grasper having an open configuration and a grasping configuration, wherein the grasper is biased to the open configuration, and wherein when the grasper is in the open configuration, the tissue fastener is disconnected from any structure within the flexible tube;
   wherein a sharp distal end of the distal member is configured to puncture a tissue wall when the tissue fastener protrudes from the flexible tube.

2. The delivery system of claim 1, further comprising a device for folding two walls of tissue together.

3. The delivery system of claim 2, wherein the tube is positioned in a lumen of the device.

4. The delivery system of claim 1, wherein the tube has a length sufficient enough to extend out of a body.

5. The delivery system of claim 1, wherein the tube includes a sharp cutting edge formed at its distal end.

6. The delivery system of claim 1, wherein the tube is configured to accommodate multiple tissue fasteners.

7. The delivery system of claim 1, further comprising an actuation means for the grasper at a proximal end of the tube.

8. The delivery system of claim 1, further including a sheath covering the tube to puncture through tissue.

9. The delivery system of claim 1, wherein the flexible tube includes a curved distal portion.

10. A delivery system configured for deployment of an expandable tissue fastener, comprising:
    a tissue fastener having a proximal member configured to expand from a delivered state to a deployed state, a distal member configured to expand from a delivered state to a deployed state, and an elongate connecting member connecting the proximal member to the distal member;
    a flexible tube having a lumen configured to accommodate the tissue fastener in a contracted state;
    a pusher for guiding the tissue fastener along the lumen of the tube; and
    a coupling system coupled to a distal end of the pusher and configured to grasp the tissue fastener, the coupling system including a pair of arms biased to an open configuration, wherein when the arms of the coupling system are in the open configuration, the tissue fastener is disconnected from any structure within the flexible tube;
    wherein a sharp distal end of the distal member is configured to puncture a tissue wall when the tissue fastener protrudes from the flexible tube.

11. The delivery system of claim 10, wherein the pair of arms are fixedly connected to the distal end of the pusher, and each arm of the pair of arms includes a bent hook at a distal end of each arm.

12. The delivery system of claim 10, wherein the pair of arms are biased apart from each other external the lumen of the flexible tube.

13. The delivery system of claim 10, wherein the pair of arms are contracted towards each other within the lumen of the flexible tube.

14. The delivery system of claim 13, wherein the pair of arms grasp the tissue fastener when the pair of arms are contracted towards each other.

15. A delivery system configured for deployment of an expandable tissue fastener, comprising:
    a tissue fastener having a proximal member configured to expand from a delivered state to a deployed state, a distal member configured to expand from a delivered state to a deployed state, and an elongate connecting member connecting the proximal member to the distal member;
    a flexible tube having a lumen configured to accommodate the tissue fastener in a contracted state;
    a pusher for guiding the tissue fastener along the lumen of the tube;
    a coupling system coupled to a distal end of the pusher and configured to grasp the tissue fastener, wherein the coupling system includes a pair of arms biased apart from each other, and
    wherein the tissue fastener is fixedly connected to the pusher within the lumen of the flexible tube and is disconnected from any structure within the flexible tube when a portion of the coupling system exits the lumen of the flexible tube, wherein the exiting of the portion of the coupling system from the lumen causes the disconnection;
    wherein a sharp distal end of the distal member is configured to puncture a tissue wall when the distal member protrudes from the flexible tube.

16. The delivery system of claim 15, wherein the pair of arms are contracted towards each other within the lumen of the flexible tube.

17. The delivery system of claim 16, wherein the pair of arms grasp the tissue fastener when the pair of arms are contracted towards each other.

18. The delivery system of claim 15, wherein the pair of arms are biased apart from each other when the arms exit the lumen of the flexible tube.

19. The delivery system of claim 18, wherein the pair of arms release the tissue fastener when the pair of arms are biased apart from each other.

20. A delivery system configured for deployment of an expandable tissue fastener, comprising:
    a tissue fastener having a proximal member configured to expand from a delivered state to a deployed state, a distal member configured to expand from a delivered state to a deployed state, and an elongate connecting member connecting the proximal member to the distal member;
    a flexible tube having a lumen configured to accommodate the tissue fastener in a contracted state;
    a pusher for guiding the tissue fastener along the lumen of the tube; and a coupling system coupled to a distal end of the pusher and configured to grasp the tissue fastener, wherein the coupling system includes a pair of arms, and wherein each of the pair or arms includes a bent hook at a distal end of each arm, wherein the coupling system is biased to an open configuration to release the tissue fastener upon deployment of the tissue fastener, and wherein the tissue fastener is disconnected from any structure within the flexible tube upon deployment;

wherein a sharp distal end of the distal member is configured to puncture a tissue wall when the distal member protrudes from the flexible tube.

21. The delivery system of claim 20, wherein the tissue fastener is fixedly connected to the pusher within the lumen of the flexible tube and is disconnected from the pusher when a portion of the coupling system exits the lumen of the flexible tube.

22. The delivery system of claim 21, wherein the pair of arms are contracted towards each other within the lumen of the flexible tube.

23. The delivery system of claim 22, wherein the pair of arms are biased apart from each other when the arms are deployed from the lumen of the flexible tube.

\* \* \* \* \*